United States Patent
Harvey et al.

(10) Patent No.: US 6,830,939 B2
(45) Date of Patent: Dec. 14, 2004

(54) SYSTEM AND METHOD FOR DETERMINING ENDPOINT IN ETCH PROCESSES USING PARTIAL LEAST SQUARES DISCRIMINANT ANALYSIS IN THE TIME DOMAIN OF OPTICAL EMISSION SPECTRA

(75) Inventors: Kenneth C. Harvey, Dallas, TX (US); Jimmy W. Hosch, Dallas, TX (US); Neal B. Gallagher, Manson, WA (US); Barry M. Wise, Manson, WA (US)

(73) Assignee: Verity Instruments, Inc., Carrollton, TX (US)

( * ) Notice: Subject to any disclaimer, the term of this patent is extended or adjusted under 35 U.S.C. 154(b) by 186 days.

(21) Appl. No.: 10/232,987

(22) Filed: Aug. 28, 2002

(65) Prior Publication Data

US 2004/0045934 A1 Mar. 11, 2004

(51) Int. Cl.[7] .............................................. H01L 21/302
(52) U.S. Cl. ...................... 438/8; 9/16; 9/714; 216/60; 134/1.2; 134/22.11
(58) Field of Search .......................... 438/8, 9, 16, 714; 216/60, 67; 134/1.1, 1.2, 22.11

(56) References Cited

U.S. PATENT DOCUMENTS

| 5,160,402 A | | 11/1992 | Cheng | |
|---|---|---|---|---|
| 5,288,367 A | | 2/1994 | Angell et al. | |
| 5,658,423 A | | 8/1997 | Angell et al. | |
| 5,862,060 A | | 1/1999 | Murray | |
| 6,046,796 A | * | 4/2000 | Markle et al. | 356/72 |
| 6,238,937 B1 | * | 5/2001 | Toprac et al. | 438/9 |
| 2003/0186461 A1 | * | 10/2003 | Boehr et al. | 436/181 |

* cited by examiner

Primary Examiner—George A. Goudreau
(74) Attorney, Agent, or Firm—Rudolph J. Buchel, Jr.

(57) ABSTRACT

The present invention is directed to a system, method and software product for creating a predictive model of the endpoint of etch processes using Partial Least Squares Discriminant Analysis (PLS-DA). Calibration data is collected from a calibration wafer using optical emission spectroscopy (OES). The data may be non-periodic or periodic with time and periodic signals may be sampled synchronously or non-synchronously. The OES data is arranged in a spectra matrix X having one row for each data sample. The OES data is processed depending upon whether or not it is synchronous. Synchronous data is arranged in an unfolded spectra matrix X having one row for each period of data samples. A previewed endpoint signal is plotted using wavelengths known to exhibit good endpoint characteristics. Regions of stable intensity values in the endpoint plot that are associated with either the etch region or the post-etch region are identified by sample number. An X-block is created from the processed OES data samples associated with the two regions of stable intensity values. Non-periodic OES data and asynchronously sampled periodic OES data are arranged in a X-block by one sample per row. Synchronously sampled periodic OES data are arranged in the X-block by one period per row. A y-block is created by assigning a discriminate variable value of "1" to OES samples associated with the class, i.e. the etch, and assigning a discriminate value of "0" to all samples not in the class, i.e. the post-etch. A b-vector is regressed from the X- and y-blocks using PLS and is used with the appropriate algorithm for processing real-time OES data from a production etch process for detecting an endpoint.

29 Claims, 28 Drawing Sheets

FIG. 10

|   | C |
|---|---|
| N | Y (N x C) |

=

|   | V |
|---|---|
| N | X (NxV) |

|   | C |
|---|---|
| V | B (V x C) |

FIG. 11C $K$ Rows $M$ rows

| | $G_{11}$ | $G_{12}$ | $G_{13}$ | $G_{14}$ | $G_{15}$ | ... | $G_{1K}$ |
|---|---|---|---|---|---|---|---|
| $s_1$ | | | | | | | |
| $s_2$ | $G_{21}$ | $G_{22}$ | $G_{23}$ | $G_{24}$ | $G_{25}$ | ... | $G_{2K}$ |
| $s_3$ | $G_{31}$ | $G_{32}$ | $G_{33}$ | $G_{34}$ | $G_{35}$ | ... | $G_{3K}$ |
| $s_4$ | $G_{41}$ | $G_{42}$ | $G_{43}$ | $G_{44}$ | $G_{45}$ | ... | $G_{4K}$ |
| $s_5$ | $G_{51}$ | $G_{52}$ | $G_{53}$ | $G_{54}$ | $G_{55}$ | ... | $G_{5K}$ |
| $s_6$ | $G_{61}$ | $G_{62}$ | $G_{63}$ | $G_{64}$ | $G_{65}$ | ... | $G_{6K}$ |
| ... | ... | ... | ... | ... | ... | ... | ... |
| $s_M$ | $G_{M1}$ | $G_{M2}$ | $G_{M3}$ | $G_{M4}$ | $G_{M5}$ | ... | $G_{MK}$ |

FIG. 12B

|  | U columns | | | | | | |
|---|---|---|---|---|---|---|---|
| $p_1$ | $s_1$ | $s_2$ | $s_3$ | $s_4$ | $s_5$ | ... | $s_R$ |
| $p_2$ | $s_{R+1}$ | $s_{R+2}$ | $s_{R+3}$ | $s_{R+4}$ | $s_{R+5}$ | ... | $s_{2R}$ |
| $p_3$ | $s_{2R+1}$ | $s_{2R+2}$ | $s_{2R+3}$ | $s_{2R+4}$ | $s_{2R+5}$ | ... | $s_{3R}$ |
| $p_4$ | ... | ... | ... | ... | ... | ... | $s_{4R}$ |
| $p_5$ | ... | ... | ... | ... | ... | ... | $s_{5R}$ |
| $p_6$ | ... | ... | ... | ... | ... | ... | $s_{6R}$ |
| $p_7$ - $p_{(P-1)}$ | ... | ... | ... | ... | ... | ... | ... |
| $p_P$ | $s_{M-(R-1)}$ | $s_{M-(R-2)}$ | $s_{M-(R-3)}$ | $s_{M-(R-4)}$ | $s_{M-(R-5)}$ | ... | $s_M$ |

P rows

FIG. 12C

First Class

Second Class $C^{th}$ Class

Matrix Y

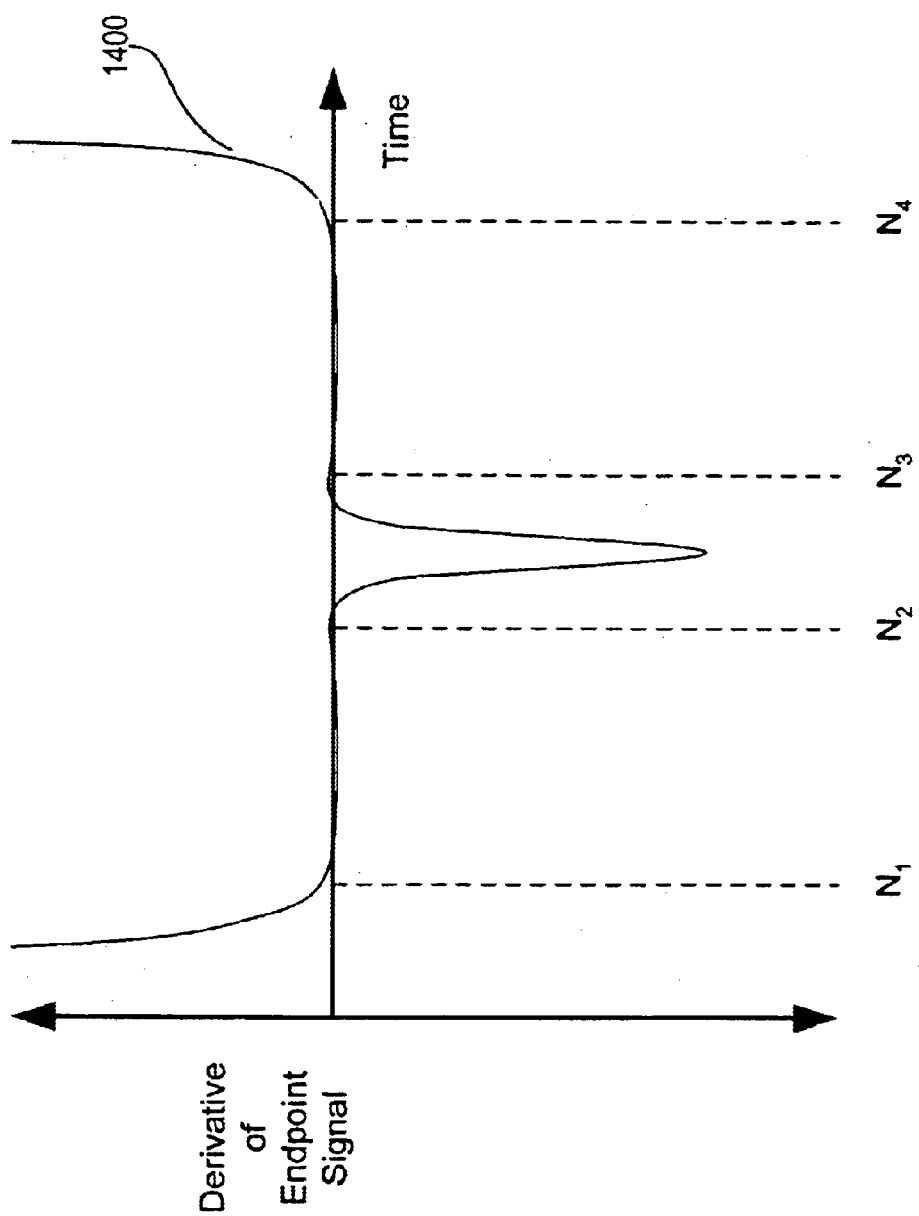

First Class

Second Class $C^{th}$ Class

Matrix Y

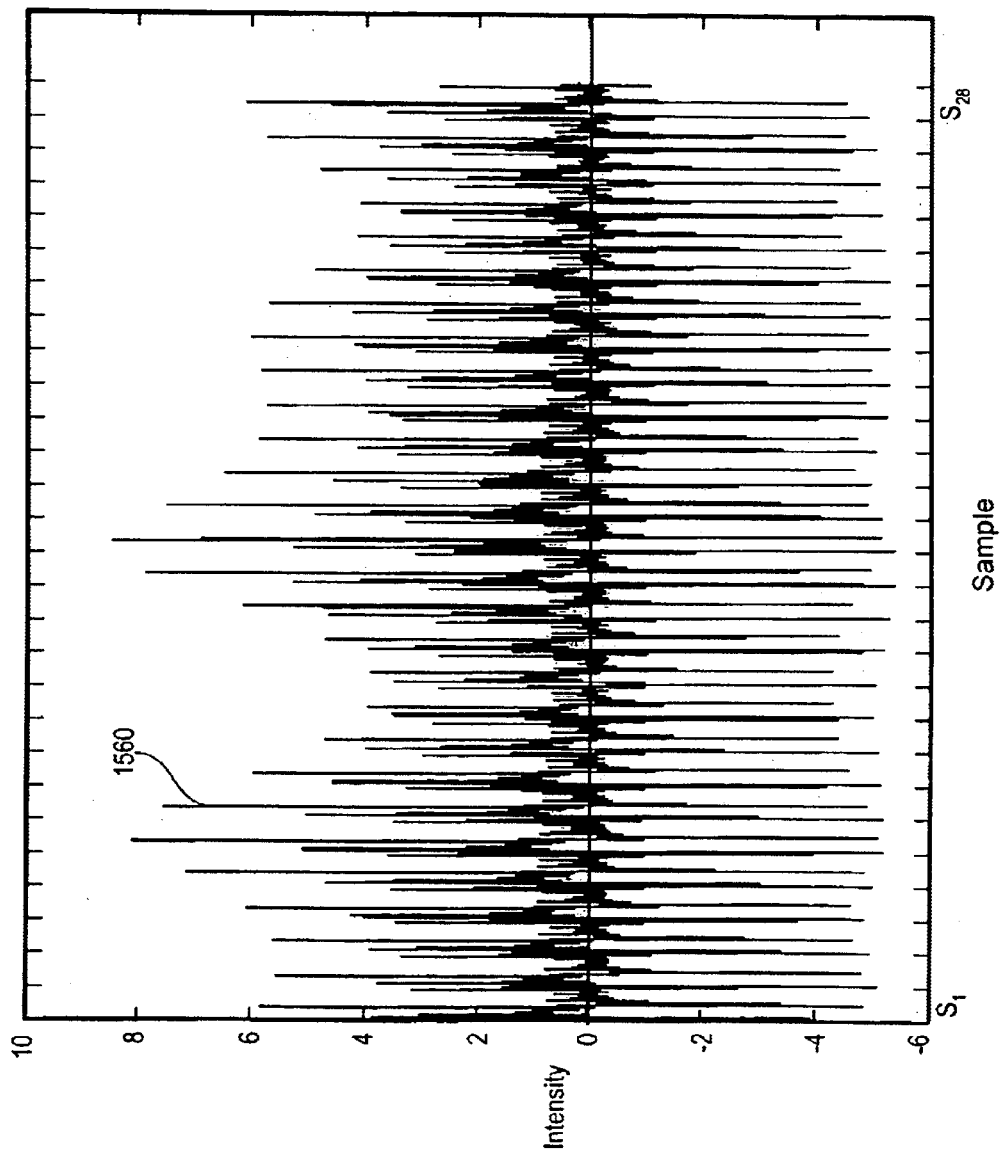

SYSTEM AND METHOD FOR DETERMINING ENDPOINT IN ETCH PROCESSES USING PARTIAL LEAST SQUARES DISCRIMINANT ANALYSIS IN THE TIME DOMAIN OF OPTICAL EMISSION SPECTRA

BACKGROUND OF THE INVENTION

1. Field of the Invention

The present invention relates to semiconductor processing, and more particularly, the present invention relates to the etch process by which semiconductor material is etched out leaving well-defined features. Still more particularly, the present invention relates to a system, method and software program product for accurately determining the changes in a signal that are indicative of an endpoint of the etching process.

2. Description of Related Art

There are many steps involved in the processing of a wafer, of which etching is one of the crucial steps. Etching is a process whereby a selected area on a wafer surface is removed so as to make a desired pattern on the surface. Plasma etching can accurately remove patterns of very small dimension on the surface of a semiconductor wafer. Reactive Ion Etching (RIE) is an etching technique in which radio frequency radiation in a low pressure gas ionizes the gas and dissociates the gas molecules into more reactive species.

FIG. 1 is a cross-sectional illustration of an etcher in which the RIE process may be performed. FIG. 1 is a diagram of an exemplary etcher intended only to aid in describing etching principles useful in understanding the description of the present invention and not intended to faithfully represent any actual etcher. Etcher 100 is a plasma etch reactor in which the RIE process is confined within chamber 102. In operation, plasma 118 is produced in chamber 102 when etching gas 122 enters reaction chamber 102 and is ionized by the application of an electric field established between cathode 110 and anode 112. As etching gas 122 is ionized into plasma 118, the respective velocity of electrons and ions are significantly different due to the difference in their masses. A typical etcher 100 uses anode 112 at ground potential and cathode 110 connected to the RF generator 114 and biased above ground. Wafer 130 is placed on the platen. Gas molecules of etching gas 122 are accelerated to the substrate surface of wafer 130 toward cathode 110 due to the difference in potential across the electrodes. Wafer 130 is bombarded with reactive positive ions created in the plasma which causes atoms of the substrate to be sputtered and usually react chemically with etching gas 122, thereby removing the top layer of material on wafer 130. The newly-formed gases 126 are removed from chamber 102 by vacuum system 125 through exhaust port 124.

The etching step of wafer production is an integral part of semiconductor manufacturing; however, equally important to accurate etching is detecting the precise point in time the etching process has ended, i.e. the "endpoint." The endpoint of the etching process is where all etched feature patterns are fully delineated and undercutting of the substrate is held to a minimum. Typically, endpoint detection mechanisms determine the endpoint of an etch process by distance determinations or by optical emission. A laser interferometer (not shown in the figure) reflects laser radiation off wafer 130 during processing and the thickness of the etched layer is determined by the interference of the reflected light. Alternatively, the optical emissions of the reaction products of the etching process are used to determine an endpoint.

Emission collection and processing mechanism 150 receives and pre-processes light emitted by the plasma into a form usable by an endpoint detection mechanism (not shown). Initially, collimating and focusing optics 152 receive light 154 from inside chamber 102 and transmit it, usually through an optical fiber, to optical emission analyzer 156. One type of optical emission analyzer 156, a monochromator, monitors the intensity of a single wavelength of light 154 from the exhaust gases and outputs signal 158 based on the intensity of the light at the wavelength being monitored. Generally, it is expected that the intensity of the light at this wavelength will change at the endpoint of the etching process, and thus the output signal 158 indicates that transition.

Accurately detecting the endpoint of an etch process by analyzing the optical emission of the reaction products depends on identifying an optimal discrete wavelength, usually associated with a reactant species, that exhibits a quantifiable intensity change of the light associated with the endpoint transition. Although the intensity of light from many reactant species decreases at the etching process endpoint, the light from some other species increases in intensity. Many factors have a detrimental effect on signal detection that must be compensated for, e.g. low amplitude of transmitted light energy 154 due to a dirty view port, spurious noise from plasma fluctuations that masks the endpoint signal, unsteady electrical fields from the electrodes, electronics malfunctions, or inaccurate optical measurements.

As fine line patterning becomes more prevalent and the percentage of area to be etched becomes smaller, accurate endpoint detection becomes more difficult. As feature sizes decrease, the percent of the wafer open area also decreases, requiring plasma etch endpoint detection systems to be more sensitive and accurate. Traditional endpoint detection systems that monitor one or two wavelengths do not generate enough information for successful endpoint determination when open areas drop below a nominal surface percentage.

In another alternative, collimating and focusing optics 152 receive light from reactant species inside chamber 102 and feeds the entire spectrum of light over a substantially broad range of wavelengths 154 to optical emission analyzer 156. Optical emission analyzer 156 is a spectrometer which is capable of monitoring multiple discrete wavelengths. Using processing functionality in optical emission analyzer 156, the operator can then select the most appropriate sets of wavelengths for reactant species associated with a particular etching process and generate output 158 from the intensities of the selected wavelengths. Monitoring intensities of multiple wavelengths gives an operator increased flexibility. The disadvantage is that the complexity increases for endpoint detection.

FIG. 1 further depicts etcher 100 as having magnets 142 on rotating magnet housing 140 for magnetically enhanced RIE etching. Magnets 142 revolve around chamber 102 causing plasma 118 to follow the magnetic field associated with magnets 142. This produces a more homogenous etch of the surface. However, magnets 142 induce one or more bright spots in plasma 118 that revolve with magnet housing 140. Optical emission analysis of the etch process becomes more challenging because the intensity of the light 154 now is periodic with the rotation of a mechanical device and is not based solely on the reactant processes. Here it is necessary for the operator to have expert knowledge of plasma chemistry and/or spectroscopy. The operator must also understand how the rotating magnets degrade the endpoint signal. Understanding how to do this optical emission analysis to find the endpoint using multiple sets of wavelength from the output of a spectrometer has been heretofore unknown.

SUMMARY OF THE INVENTION

The present invention is directed to a system, method and software product for creating a predictive model of the endpoint of etch processes using Partial Least Squares Discriminant Analysis (PLS-DA). Initially, intensity readings for discrete wavelengths in a spectrum are collected from a calibration wafer using optical emission spectroscopy (OES). Intensity values in the OES data may represent a signal that is non-periodic or periodic with time. Periodic signals may be sampled synchronously or non-synchronously with the period of a signal. Initially, the OES data is arranged in a spectra matrix X having one row for each data sample.

The OES data is processed to remove transients that occur during the startup and shutdown of the etch process. Wavelength regions are selected with desirable endpoint transition qualities, such as sharpness, and wavelengths with saturated intensity values are wholly removed from the processed OES data.

A preview endpoint signal is plotted using the selected wavelength regions and/or PCA analysis on the spectra matrix X. Regions of stable intensity values on the endpoint plot, that are associated with either the etch region or the post-etch region, are identified by sample number. An X-block is created from the processed OES data samples associated with the two regions of stable intensity values. Non-periodic OES data and asynchronously sampled periodic OES data are arranged in an X-block by one sample per row. Synchronously sampled periodic OES data are arranged in the X-block by one period per row. A y-block is created for classifying the features of the etch process by using binary partitioning; here, these features are the regions of stable intensity values associated with the etch. The y-block is created by assigning a discriminate variable value of "1" to OES samples in the class of the etch region and assigning a discriminate value of "0" to samples not in that class. A b-vector is obtained by regression from the X- and y-blocks using PLS and is validated using the processed OES data in spectra matrix X. Various other vectors are obtained from the validated b-vector and are used with the appropriate algorithm to process real-time OES data from a production etch process to detect endpoint.

BRIEF DESCRIPTION OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

FIG. 10 is a diagram illustrating the dimensions of class matrix Y, spectra matrix X and regression matrix B;

FIG. 11C depicts a folded matrix X for a more general case of measurements, wherein each row contains readings $G_{ij}$ for generalized spectra $s_i$;

FIG. 12B depicts unfolded matrix X, wherein each row contains all R number of spectra that were taken in a unique period of the signal;

FIG. 12C depicts matrix X as unfolded by period, wherein each row contains all intensity values $I_{ij}$ taken in each spectra $s_t$ for a unique period $p_k$;

FIG. 14A is an illustration of the derivative 1400 of the data for endpoint signal 1300;

FIG. 15D is a diagram illustrating b-vector 1560 which is derived from synchronously sampled periodic OES data in accordance with an exemplary embodiment of the present invention, where R OES spectra (R=28) are taken each period and each of the R spectra correspond to a magnet position on the housing on a magnetically enhanced etcher;

Other features of the present invention will be apparent from the accompanying drawings and from the following detailed description.

DETAILED DESCRIPTION OF THE INVENTION

Figure 1:
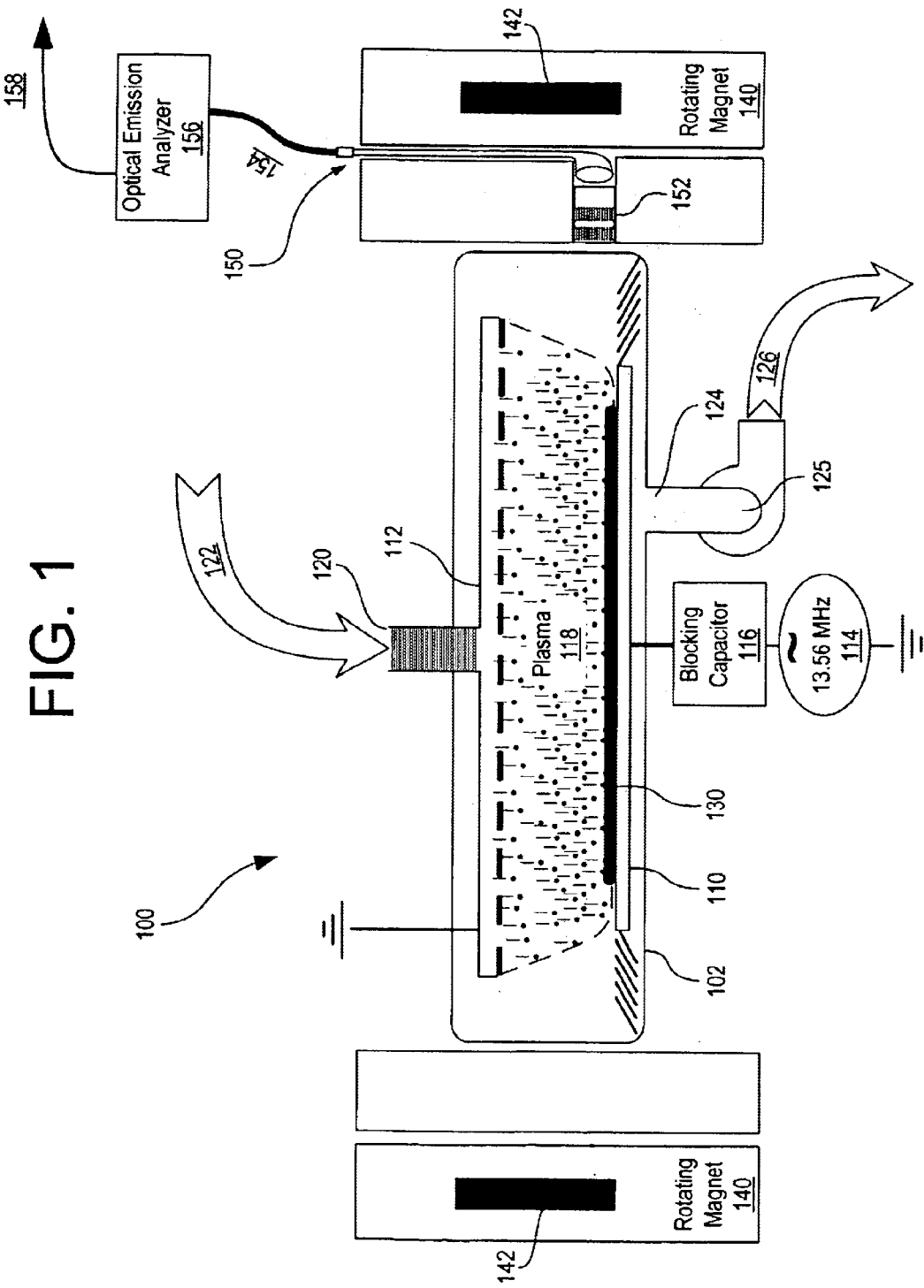
FIG. 1 is a cross-sectional diagram of an etcher in which the RIE process may be performed.
Figure 2:
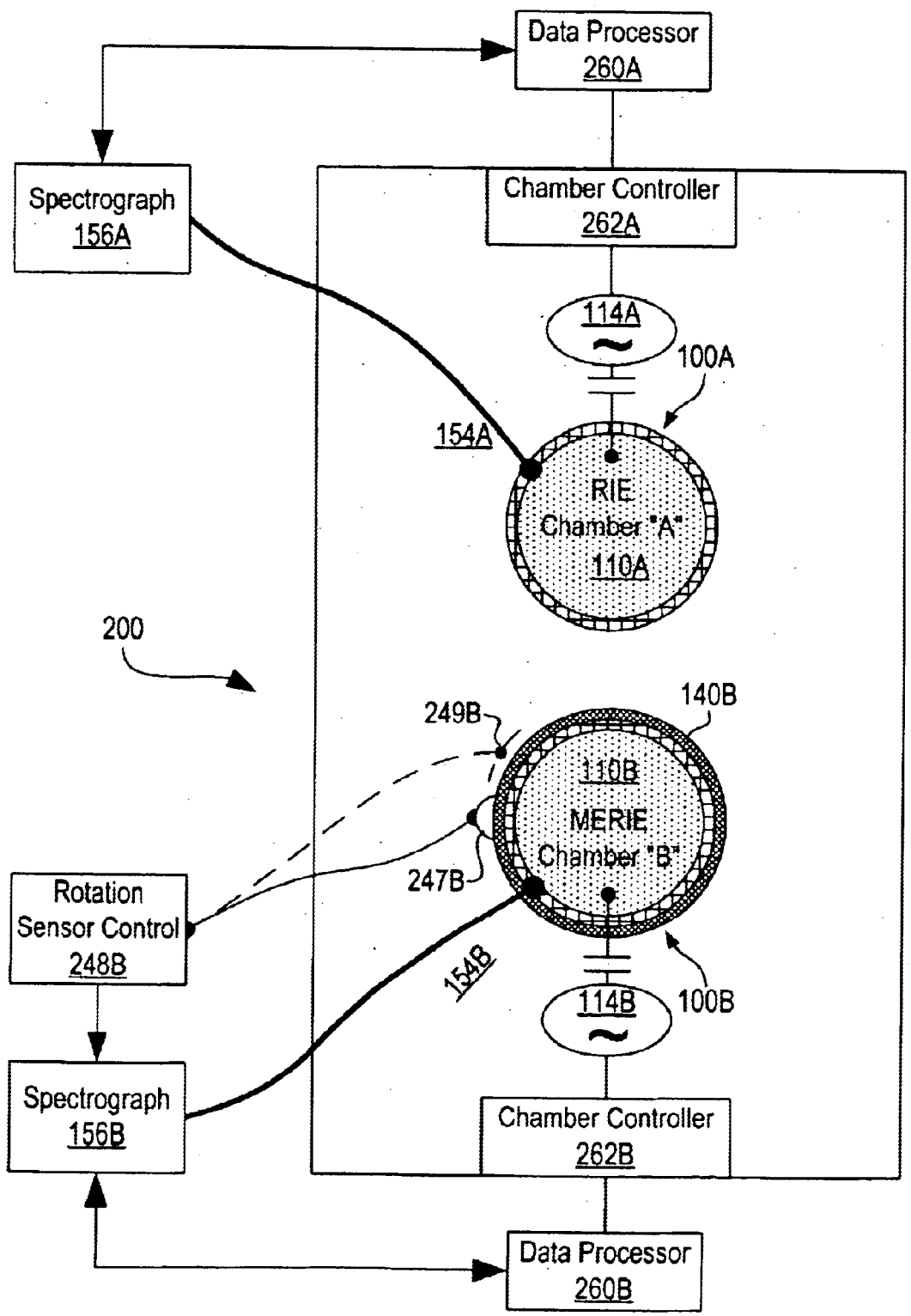
FIG. 2 is a diagram of a plasma etcher configured for data collection in accordance with an exemplary embodiment of the present invention.

FIG. 2 is a diagram of an exemplary multi-chamber etcher and is intended only to aid in describing etching principles useful in understanding the description of the present invention. Although multi-chamber etcher 200 is not intended to accurately depict an actual etcher, multi-chamber etchers, such as the P5000 Etcher available from Applied Materials in Santa Clara, Calif., are well known in the art. Multi-chamber etcher 200, as depicted, has two exemplary etch chambers, 100A and 100B. Elements associated with a particular etch chamber are identifiable by the character designation of A and B, respectively. Etch chamber 100A is RIE, while etch chamber 100B supports magnetically enhanced RIE using rotating magnets 140B. Each of chambers 100A–100B have cathodes 110A–110B, electrically connected to RF generators 114A–114B by way of blocking capacitors. Light 154A–154B is captured in each of etch chambers 100A–100B and transmitted to spectrographs 156A–156B. The relative position of rotation of rotating magnets 140B associated with etch chamber 100B is sensed using Hall-effect sensor 247B from changes in the magnet flux associated with the magnets mounted thereon. Hall-effect sensor 247B is in turn electrically coupled to rotation sensor control 248B for decoding the signals from sensor 247B. Alternatively, the orientation of rotating magnets 140B may be tracked directly by any means that measures the magnets position using magnet rotation sensor 249B, coupled likewise to rotation sensor control 248B. Rotation sensor control 248B provides orientation information to spectrograph 156B, which also receives spectra light intensities 154B from etch chamber 100B. Spectrograph 156B uses the orientation information to synchronize the data samples of the light intensity with the orientation of rotating magnets 140B.

Synchronous detection with CCD detectors in spectrograph 156B has been demonstrated to improve the signal-to-noise ratio as discussed in "System to phase lock a self-scanning photodiode array to an external signal" by Harvey, et al., Rev. Sci. Instrum. 63 (3), March 1992, pp. 1991–1998, incorporated by reference herein in its entirety.

The light intensity 154B is sampled at discrete wavelengths by spectrograph 156B and passed to data processor 260B as intensity values for each discrete wavelength. An exemplary spectrograph may be any type having a high-grade sensor array and being capable of interfacing with a data processor such as the SD1024 Smart Detector Spectrograph available from Verity Instruments, Inc. in Carrollton, Tex.

In operation, both RIE etch chambers 100A–100B are loaded with wafers and evacuated. Rotating magnets 140B are set in motion for chamber 100B. Etch gases are put into chambers 100A–100B and etching pressure is established. Spectrographs 156A–156B sample optical emission spectra by optical emission spectroscopy (OES). During calibration, which we discuss below, spectrographs 156A–156B send OES data to data processors 260A–260B for storage. During production, spectrographs 156A–156B may send OES data to data processors 260A–260B for storage. During production, data processors may send in real time endpoint data to chamber controllers 262A–262B for endpoint control of the etch process.

Figure 3:
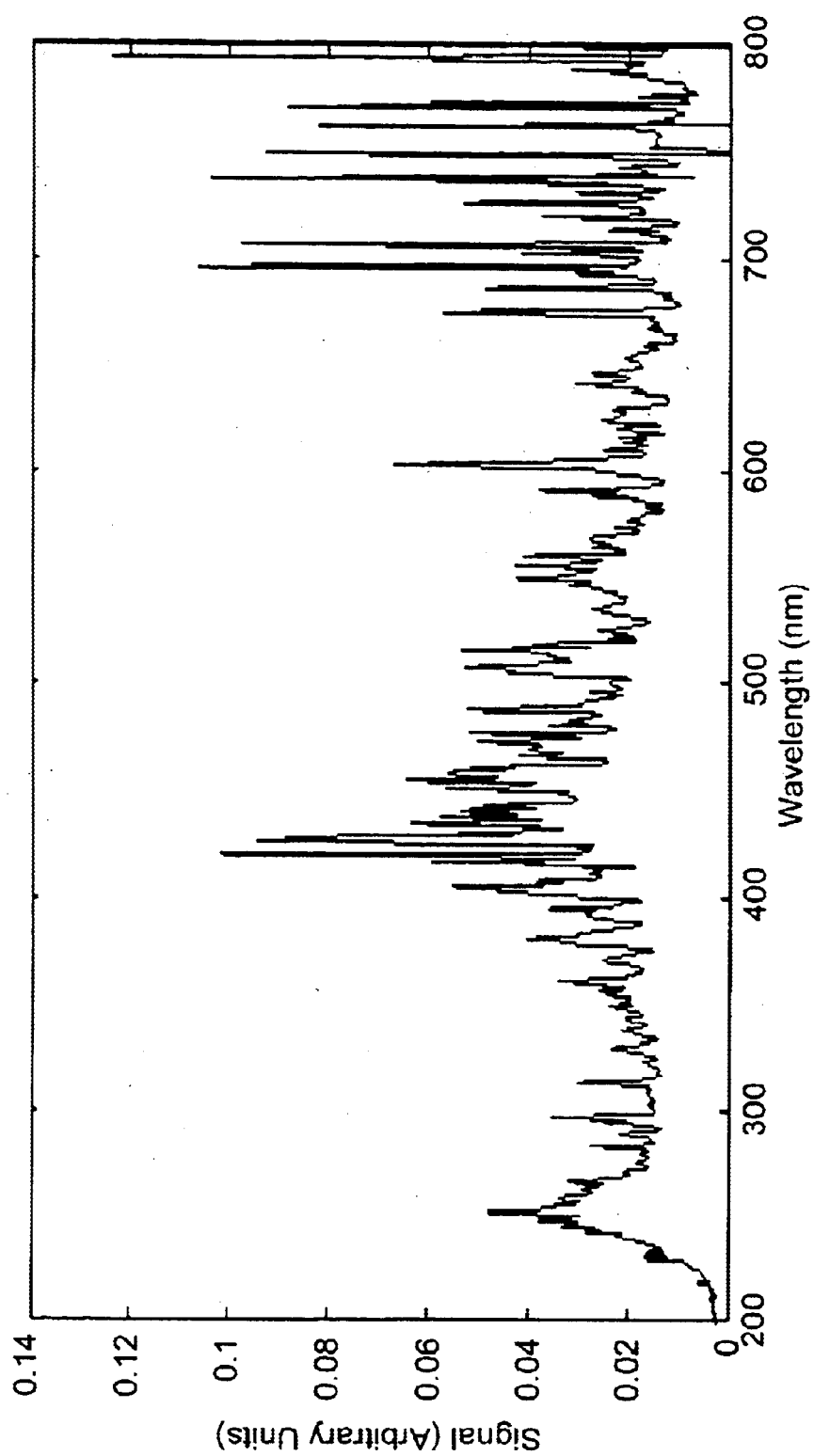
FIG. 3 is an illustration of an exemplary spectrum of intensity values taken at a sample time $T_j$, as might be measured by one of spectrographs 156A or 156B during an etch process.
Figure 4:
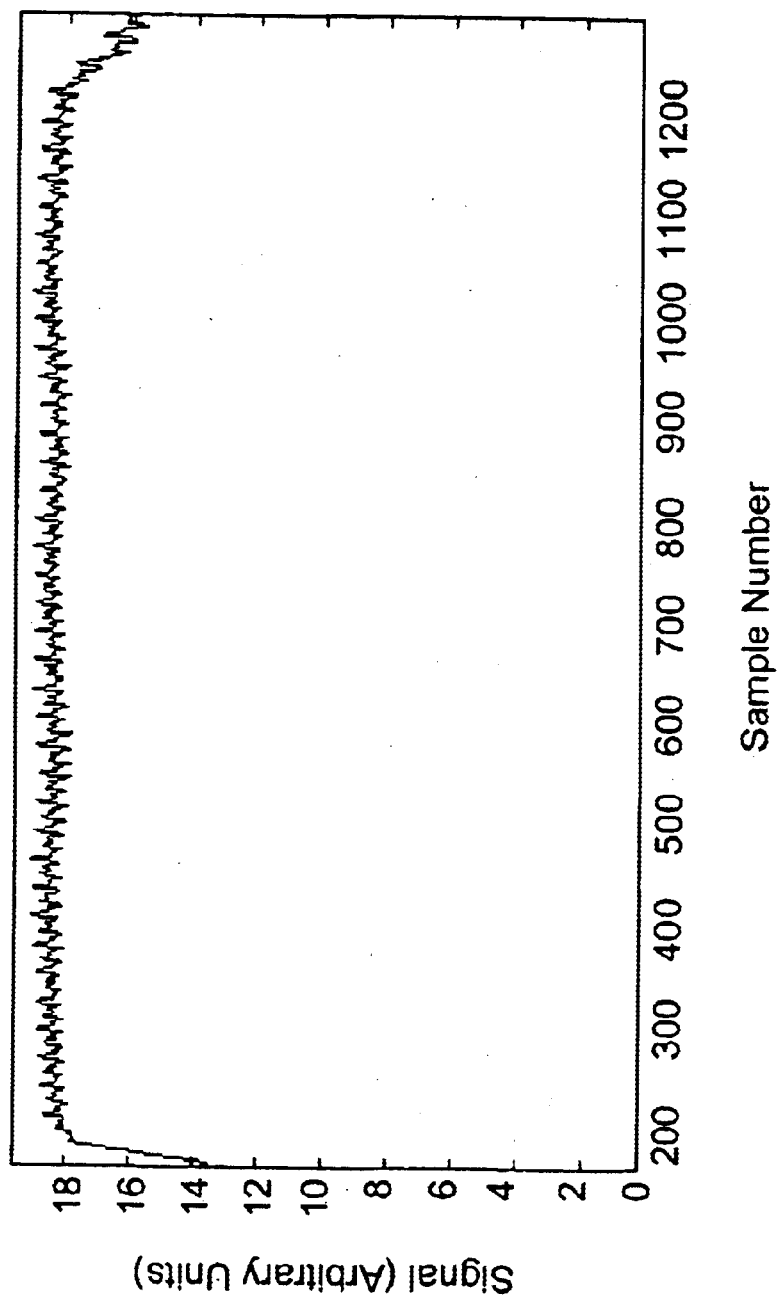
FIG. 4 illustrates the signal intensity of an exemplary 325 nm wavelength over a time interval corresponding to sampling times for samples 0–1300.
Figure 5:
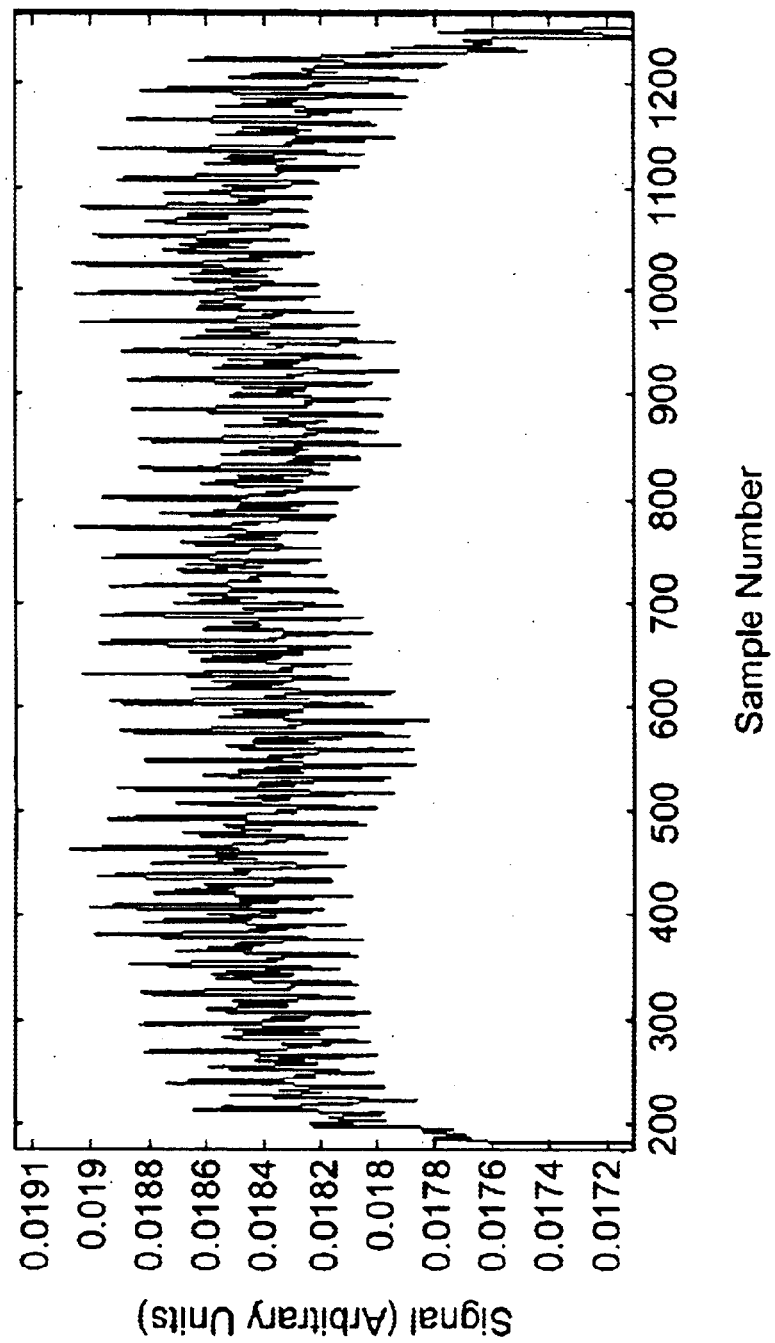
FIG. 5 is an illustration of the intensity signal shown in FIG. 4 over the identical time interval for the 325 nm wavelength with a vertical scale magnified to 0.0172–0.0191 arbitrary units.
Figure 6:
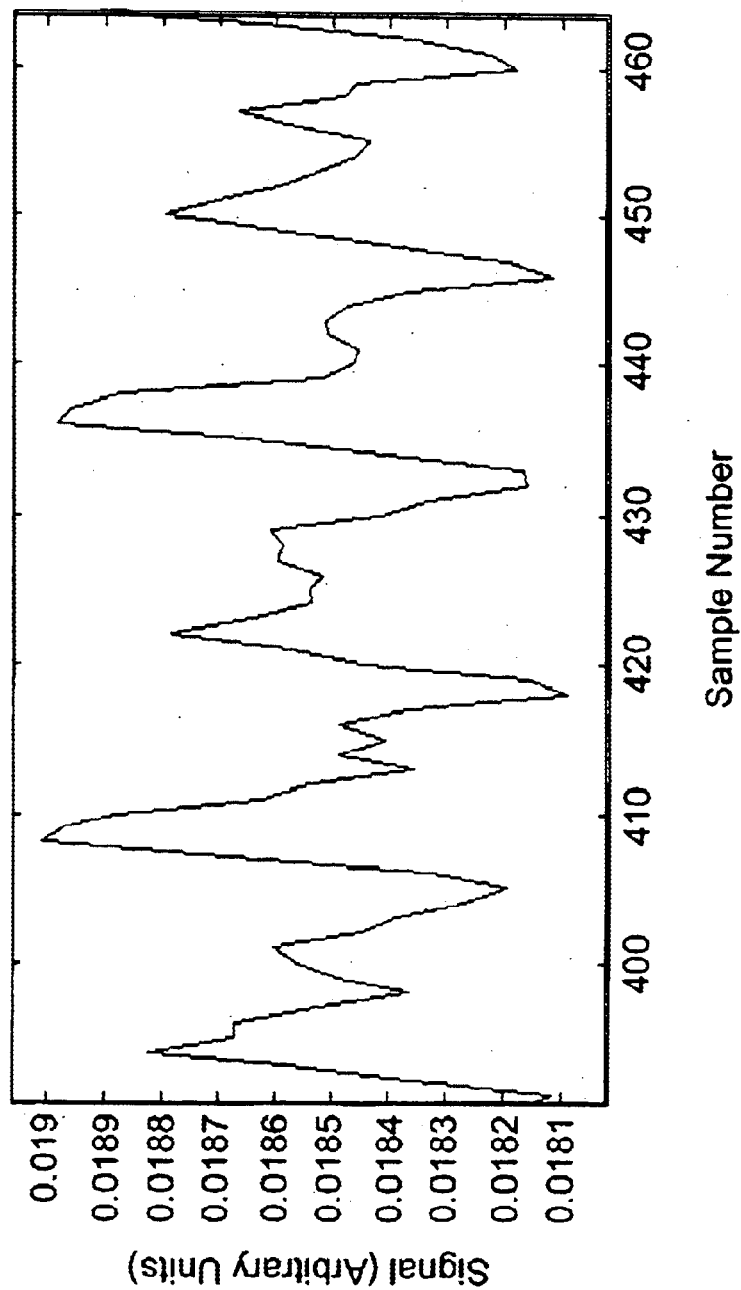
FIG. 6 is another illustration of the intensity signal shown in FIG. 4 for the 325 nm wavelength displayed with approximately the same intensity scale as in FIG. 5 but with a time interval of less than one hundred samples.

FIG. 3 is an illustration of an exemplary spectrum of intensity values as might be measured by one of spectrographs 156A or 156B during an etch process. FIG. 4 illustrates for magnetically enhanced RIE the signal intensity at an exemplary 325 nm wavelength over a time interval corresponding to sampling times for samples 0–1300. Variations in signal intensity can be clearly seen in FIG. 4. FIG. 5 is an illustration of the intensity signal shown in FIG. 4 over the identical time interval for the 325 nm wavelength; however, the intensity signal in FIG. 5 is magnified by scaling the intensity between 0.0170 and 0.0191 arbitrary signal units. The variations in signal intensity seen in FIG. 4 are more apparent in FIG. 5. FIG. 6 is another illustration for the 325 nm wavelength displayed at approximately the same intensity scale as shown FIG. 5, but only sample numbers between 390 and 465 are depicted in FIG. 6.

Figure 7:
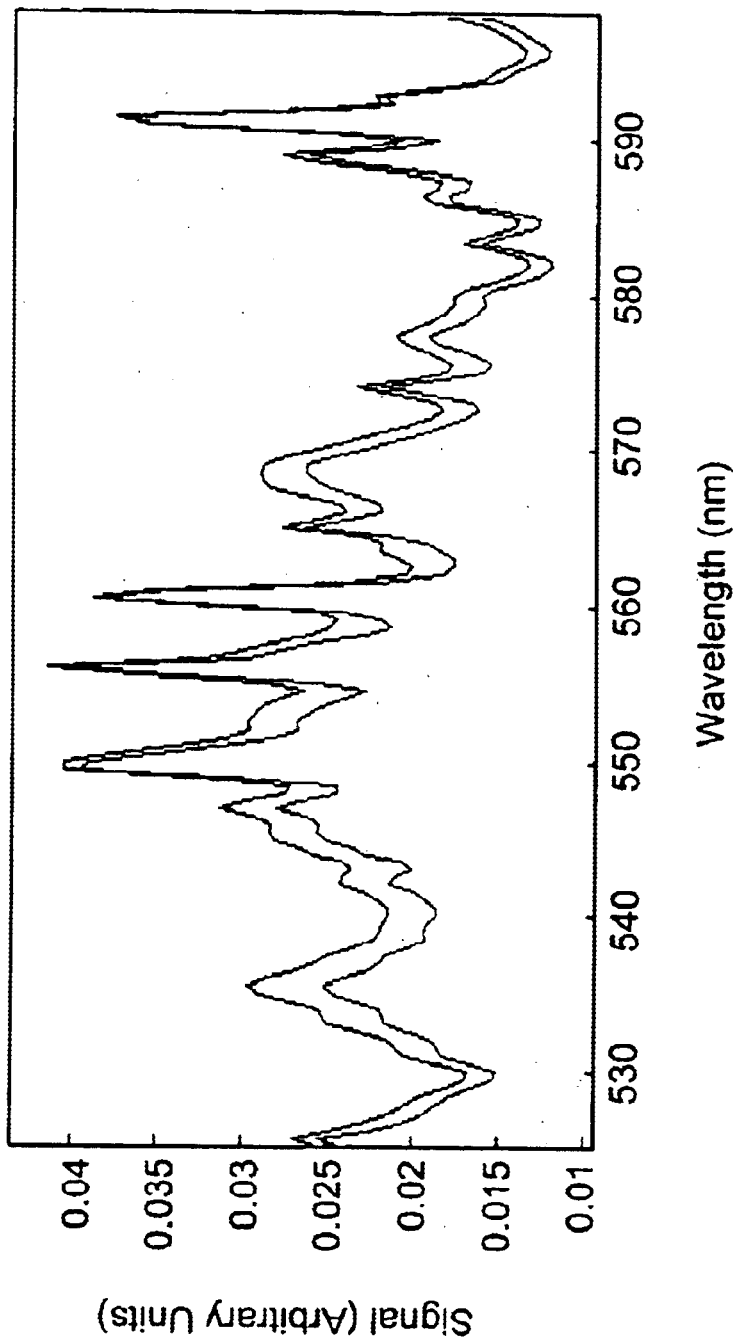
FIG. 7 is an illustration that compares the spectral intensity values of sample 409 and sample 419.
Figure 8:
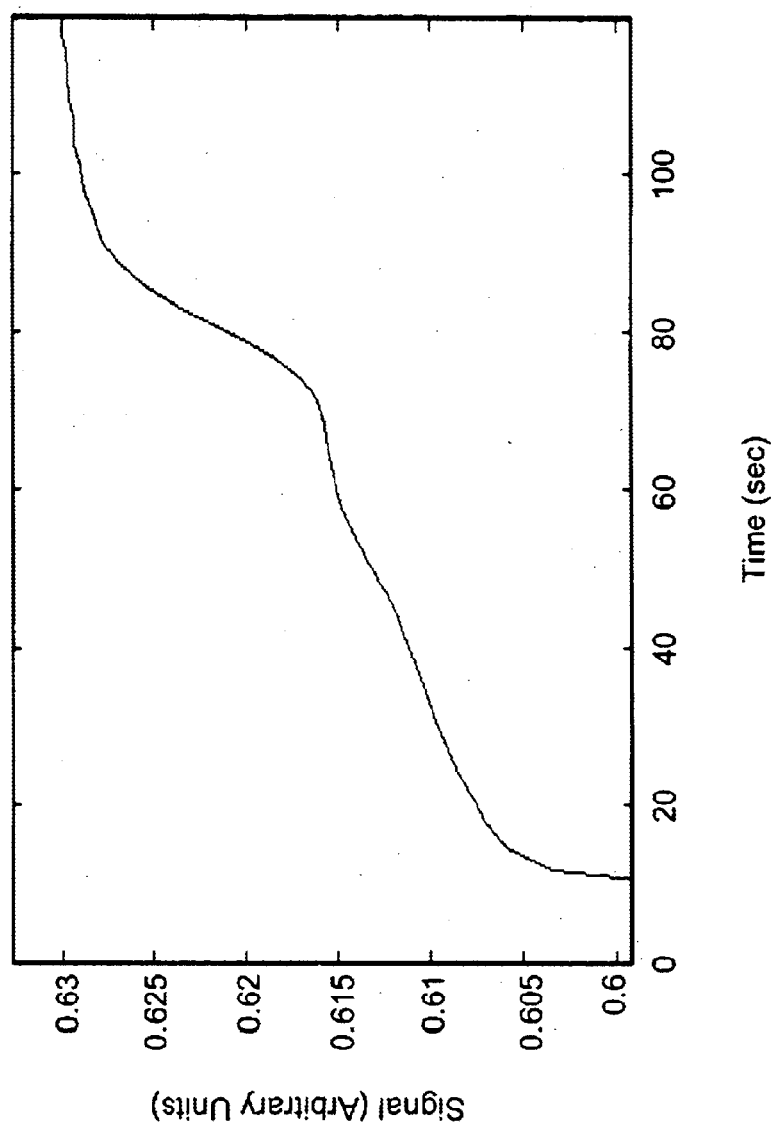
FIG. 8 is a plot of an exemplary endpoint signal using wavelength regions with desirable endpoint transition qualities and data from a contact etch of a production wafer with 4% open area.
Figure 9:
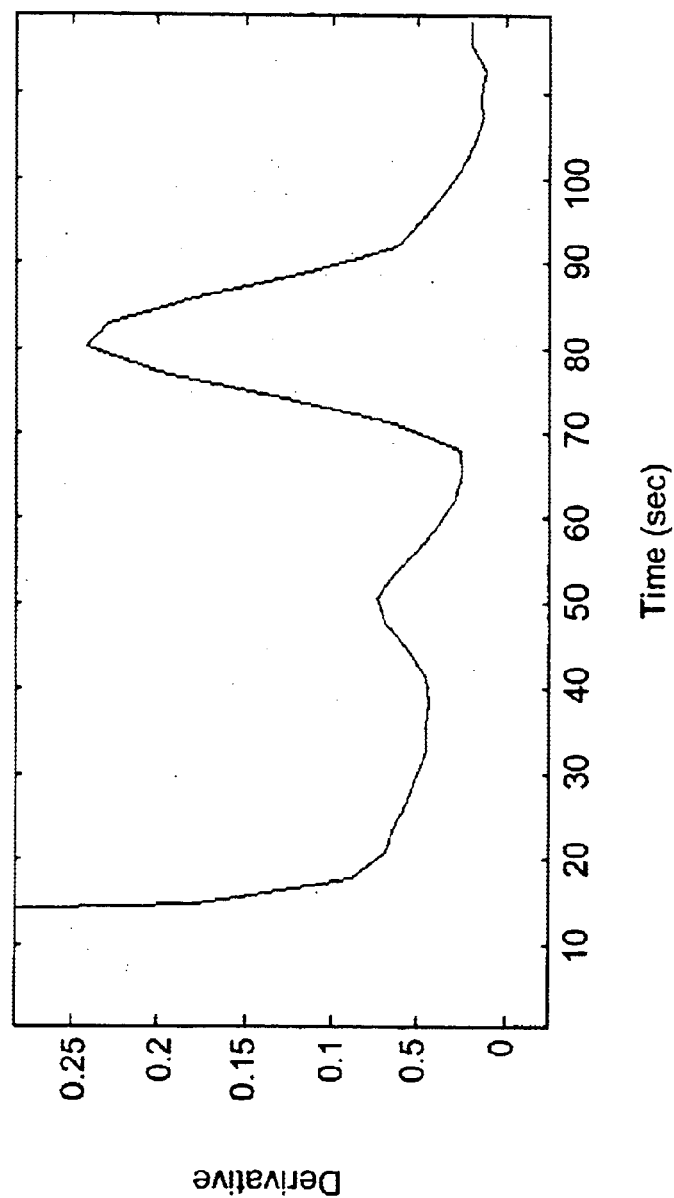
FIG. 9 is a plot of the derivative of the endpoint signal depicted in FIG. 8.

FIG. 7 is an illustration of a comparison of the spectra intensity values of the $409^{th}$ sample and $419^{th}$ sample. Note that a change in the intensity values of some wavelengths in the spectra has occurred between the $409^{th}$ and $419^{th}$ sample times. However, it cannot be known whether the change in intensity values between the two spectra samples is a result of emissions from an etch process, periodic noise caused by the rotating magnets or a combination of the two. It should also be apparent that the change in intensity values between the $409^{th}$ and $419^{th}$ sample is greater in some wavelength regions of the spectra than in others. Endpoint transitions are more difficult to detect in wavelength regions that lack desirable endpoint transition properties, such as sharpness of the transition. Moreover, even if wavelength regions are selected with desirable endpoint transition properties, the transition might be masked by the periodic noise during the endpoint transition. The challenge is to select wavelength regions with desirable endpoint transition properties from the spectra, even if the regions are not contiguous, and diminish the effect of periodic noise on endpoint detection. FIG. 8 is a diagram of a plot of an exemplary endpoint signal using wavelength regions with desirable endpoint transition properties. The endpoint transition region can clearly be seen occurring between 70 and 90 seconds. FIG. 9 is a diagram of the derivative of the endpoint signal depicted in FIG. 8 showing the region of change associated with the endpoint at approximately the same time interval.

The exemplary embodiments described below were selected and described in order to best explain the principles of the invention and the practical application, and to enable others of ordinary skill in the art to understand the invention for various embodiments with various modifications as are suited to the particular use contemplated. The particular embodiments described below are in no way intended to limit the scope of the present invention as it may be practiced in a variety of variations and environments without departing from the scope and intent of the invention. Thus, the present invention is not intended to be limited to the embodiment shown, but is to be accorded the widest scope consistent with the principles and features described herein.

The present invention is directed to a method for creating a predictive model of the endpoint of etch processes using Partial Least Squares Discriminant Analysis (PLS-DA). PLS-DA is a technique of statistical pattern recognition in which samples are classified. The present process involves the steps of collecting calibration data, creating a predictive model using the PLS-DA algorithm and applying the predictive model to data from an etch process for real-time endpoint detection. The method uses the calibration data, which are intensity measurements from an etch process on a calibration wafer, to identify the appropriate wavelengths for calculating an endpoint signal for a particular etch process. A suitable calibration set must contain an identifiable endpoint for the etch process. A training data set is identified in the calibration data set by dividing the calibration data samples into classes based on their association with endpoint features. The training data set is then arranged in a matrix and is the predictor block in the PLS calculation of a predictive model. The response matrix is created by assigning binary variable values to represent the classes. The predictive model can be verified by generating an endpoint using the full calibration data set and comparing the predicted endpoint with the known endpoint. Finally, the predictive model can make real-time endpoint predictions for etch processes that are similar to those for the calibration wafer.

The present process for creating a predictive model using PLS-DA is adaptable. Real-time endpoint detection can be done for a variety of data and data collection conditions by modifying the calibration process. Signals measured during an etch process may be periodic or non-periodic. Periodic signals have intensity values that repeat during some regular time interval, $T_p$, while non-periodic signals do not repeat during any regular time interval. The time interval, $T_p$, is the period of the signal. For the purposes of discussing the present invention, it will be assumed that the intensity of the periodic signal results from two things, an etch reaction and the carrier gas. The source or nature of the periodic behavior is relatively unimportant for application of the present invention. However, it is assumed that the period of the intensity remains constant.

Periodic signals may be detected either synchronously or non-synchronously. Synchronous detection may be done with the signal itself in a phaselock technique or with a timing signal has the period of the signal. Since the frequency and amplitude of the synchronously detected periodic component are both stable, the portion of the intensity values attributable to the periodic component are static for each similarly positioned sample of every sample period. Therefore, non-synchronous detection of a periodic signal has intrinsically more noise than synchronous detection. The present PLS-DA method will be discussed below with regard to periodic signals, sampled synchronously or asynchronously, and non-periodic signals.

The PLS-DA algorithm incorporates both Partial Least Squares regression and Discriminant Analysis. Partial Least Squares (PLS) is a projection method for the calculation of regression models for multivariate data. This method is sometimes called Projections to Latent Structures. Discriminant Analysis divides samples into classes based on certain features of the samples and associates discriminant variables with the classes in a Y-block. For endpoint detection, PLS-DA is an improvement over existing methods that use Principal Component Analysis (PCA). In the present application, the classes of interest are regions of stable intensity values associated with different regions of etch. However, transition regions with a corresponding class variable appropriately set between the extremes could be used.

In PCA, the variation of the data is described as a few principal components, or latent variables, that are orthogonal to each other. This can reduce the dimensionality of the data. PCA can follow process dynamics or detect faults. In PCA, the latent variables of greatest variance are found. However, when the noise sources are large or the signal is small, the latent variables of greatest variance may be noise sources with large variance. With regard to an etch process, the noise can obscure the desired endpoint signal. It can sometimes find a transition in the signal that is not the true endpoint because it looks for any type of change, not just changes associated with the endpoint. This results in ambiguous interpretations of endpoint changes or slow endpoint transitions. Thus, PCA is often unsuitable for endpoint detection.

In the present description of an exemplary embodiment, the following conventions for notation are observed. Normal, non-bold characters in italics, including upper case characters, are scalars. They can refer to single data elements, or can have a special meaning as is explained in the text. Examples are vector elements, e.g. $v_i$, matrix elements, e.g. $x_{ij}$, and indices, e.g., i,j and k. Capital, non-bold characters are index limits, e.g., K and N. Bold, lower case characters are vectors, e.g. x and y. The elements of x may be $x_i$, i=1,2, . . . , N. Bold, upper case characters are two-way arrays or matrices, e.g. X and Y. Vectors may be expressed in terms of scalars. A 1×N row vector u, which is composed of scalars $u_i$, is written u=[$u_1$, $u_2$, . . . , $u_N$]. A N×1 column vector v, which is composed of scalars $v_i$, is written v=[$v_1$; $v_2$; . . . ; $v_N$]. In other words, objects in a row are separated by commas, and objects in a column are separated by semicolons. Matrices may be expressed in terms of scalars, vectors, or other matrices. A N×K matrix $M_1$, which is composed of 1×K row vectors $u_i$, is written as $M_1$=[$u_1$; $u_2$; . . . ; $u_N$]. A K×N matrix $M_2$, which is composed of K×1 column vectors $v_i$, is written as $M_2$=[$v_1$, $v_2$, . . . , $v_N$]. A 2×12 matrix $M_3$, which is composed of 2×3 matrices $P_i$, is written as $M_3$=[$P_1$, $P_2$, $P_3$, $P_4$]. A 8×3 matrix $M_4$, which is composed of 2×3 matrices $P_i$, is written as $M_4$=[$P_1$; $P_2$; $P_3$; $P_4$].

PLS was developed by H. Wold in Quantitative Sociology, ed. by H. M. Blalock, et al. Academic Press Inc., New York, 307–357(1975) and extended to chemistry by S. Wold, et. al., in Matrix Pencils, ed. by A. Ruhe, et al. Springer-Verlag, Heidelberg, 286–293 (1983), which are incorporated herein by reference in their entirety. It is an extension of PCA for regression analysis. The objectives of PLS are to find how a predictor matrix X is related to a response matrix Y by a regression matrix B and to create a predictive model:

$$XB=Y. \qquad (1)$$

PLS finds the latent structure in the predictor matrix X and in the responses Y. This is a dimensionality reduction of the data matrix X. It maximizes the covariance between the variances of X and the variances of Y. PLS has an advantage over PCA in that Y may be specified so as to more physically describe the data. A numerical algorithm for PLS is SIMPLS, which was developed by S. de Jong in SIMPLS: An Alternative Approach To Partial Least Squares Regression, Chemometrics and Intelligent Laboratory Systems, 18 (1993) 251–263 which is incorporated herein by reference in its entirety. Instances of Y are predicted from the product of measured vectors in X with the regression matrix B:

$$Y=XB \qquad (2)$$

In some cases, Multiple Linear Regression (MLR) could estimate B. However, there is a significant amount of correlation in X for OES data which can result in a system that is rank deficient or nearly rank deficient. The result is a poor or unstable estimate of B. Also, if there are more variables than samples, which is typical for OES data, then the matrix X is rank deficient and MLR is not an option. Therefore, PLS is superior because it can handle rank deficient systems.

Discriminant Analysis (DA) divides samples into classes based on certain features of the samples and associates variables with the classes. The purpose of creating classification or pattern recognition models is to detect these features in measurement samples and assign the samples to the correct classes.

PLS-DA is a supervised classification method that uses regression for multivariate problems. PLS-DA was first described by M. Sjostrom, et al., in Proceedings of PARC in Practice, Amsterdam, June 19–21, Elsevier Science Publishers B.V., North-Holland (1986) and PLS discrimination plots, in Pattern Recognition in Practice II, Elsevier., Amsterdam, 1986, pp. 461–470, and by L. Stahle, et al. in Journal of Chemometrics 1, 185–196 (1987), which are incorporated herein by reference in their entirety. PLS-DA is a synthesis of PLS and DA. An inverse least squares model can be used for one-class data $$Xb=y \qquad (3)$$

where X is the spectra matrix of the calibration data and y is the class vector which describes the class membership of the observations. The regression vector b is the direction in X that is parallel to y and orthogonal to other types of variations. This is important since there can be a significant amount of variance in X that is not associated with endpoint. Therefore, the regression analysis identifies wavelengths that directly relate to the endpoint transition.

Figure 10:
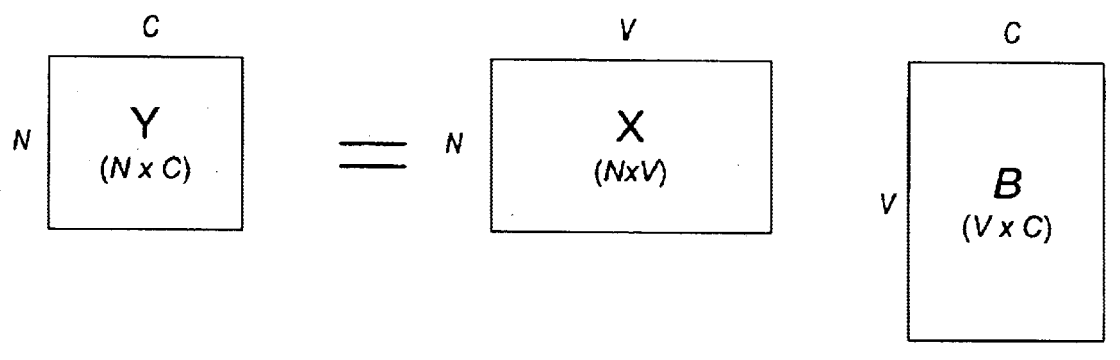

Most embodiments described below will be cases involving regression analysis which identify wavelengths that contribute to a single endpoint. Therefore, the measurement samples will contain only a single feature resulting in a single class, and so b and y will be vectors. However, the present PLS-DA algorithm is exceptionally flexible allowing for the creation of predictive models for accurately detecting C endpoints, where C>1. In those cases, the measurement samples will contain C features resulting in C classes and the regression analysis identifies wavelengths that directly relate to C endpoints. Thus, in general, the matrix X is a N×V matrix, the regression matrix B is a V×C matrix and the class matrix Y is a N×C matrix. The dimensions of class matrix Y, regression matrix B and spectra matrix X in equation (2) are pictorially represented in FIG. 10. Also, if there are C classes, one may create a separate single-class model for the each of the C classes. This will yield C different b-vectors $b_i$, i=1, . . . , C.

PLS-DA finds the direction in X space that best describes the difference between the classes. The N×V matrix X is the predictor block in the calculations of a calibration model for a known time variation Y using PLS. After collecting the calibration data, such as OES data, the intensities of the spectra that are measured are placed in the spectra matrix, X. These intensities are the descriptors of the system.

Figure 11B:
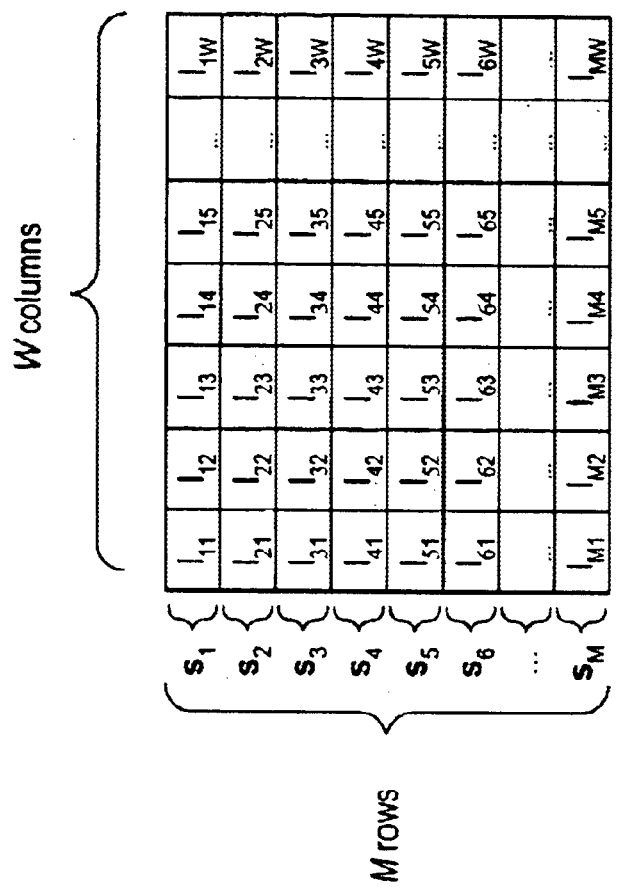
FIG. 11B depicts a folded spectra matrix X, wherein each row contains intensity values $I_{ij}$ for a unique spectra $s_i$.
Figure 11A:
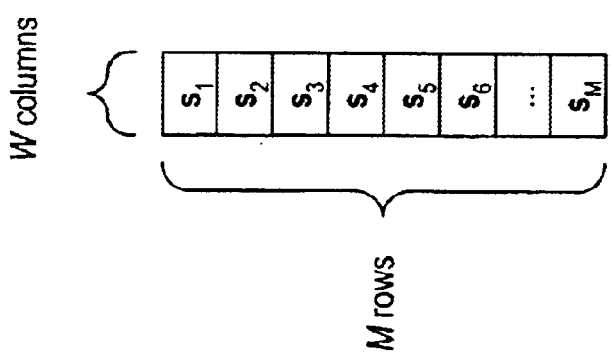
FIG. 11A depicts each row of a folded matrix X with W columns and M rows.

The measurements of the spectra are done at M equally spaced times, $T_i$, with indices, i=1, . . . , M. The time $T_s$ between measurements is called the sample interval. It is assumed that the time required for making the measurements of the intensities at the various wavelengths in a spectrum, or the integration time $T_o$, is small compared to $T_s$. Thus, $T_s \gg T_o$. However, the present process will perform equally well in cases where the integration time $T_o$ is not small compared to the sample interval $T_s$, i.e. $T_s \square T_o$. For a measurement M consisting of M spectra $s_i$, M=[$s_1, s_2$; . . . ; $s_M$]. FIG. 11A depicts such a M×W matrix where each row holds the data from one sample time. The spectra $s_i$ has intensities $I_{ij}$, such that $s_i$=[$I_{i1}, I_{i2}, I_{i3}, \ldots I_{iW}$]. Each intensity readings $I_{ij}$ corresponds to a discrete wavelength $\lambda_j$, j=1,2, . . . , W.

Depending upon whether the data is periodic or non-periodic, and whether the periodic data is detected synchronously or asynchronously, the data in measurement M are arranged in the matrix X in one of two ways in preparation for PLS regression.

In the first way, each row of the matrix X holds a single spectrum taken at a unique sample time. Matrix X has M rows and W columns. This matrix is described as folded and will be referred to as such hereinafter. FIG. 11B depicts a spectra matrix X as folded, wherein each row contains one spectrum $s_i$, which consists of a plurality of intensity values $I_{i1}, I_{i2}, \ldots I_{iW}$ and the W intensity readings in spectrum $s_i$ are taken at discrete wavelengths $\lambda_1, \lambda_2, \ldots, \lambda_W$.

Creating a predictive model for endpoint detection, or a predictive model of any other type of event detection, need not be based solely on OES intensity data and may consist of readings other than spectra intensity values. Matrix X may be created from any type of measurement where the measurement M comprises a plurality of measurements when the readings $G_{ij}$ are taken simultaneously, where $s_i$=[$G_{i1}, G_{i2}, \ldots G_{iK}$]. Of course, a valid predictive model requires that the signal obtained from calibration data have some feature that correlates to the event to be detected using the predictive model. FIG. 11C depicts matrix X as folded for this more general case.

As should be apparent from the discussion of the folded matrix X, each row of the folded matrix X consists of all simultaneously recorded sample readings taken at time $T_i$. Therefore, the training data may be arranged in a folded matrix X whether or not the calibration data is periodic. However, as will be discussed below, noise must be filtered from a periodic signal prior to creating and regressing the folded matrix X.

Figure 12A:
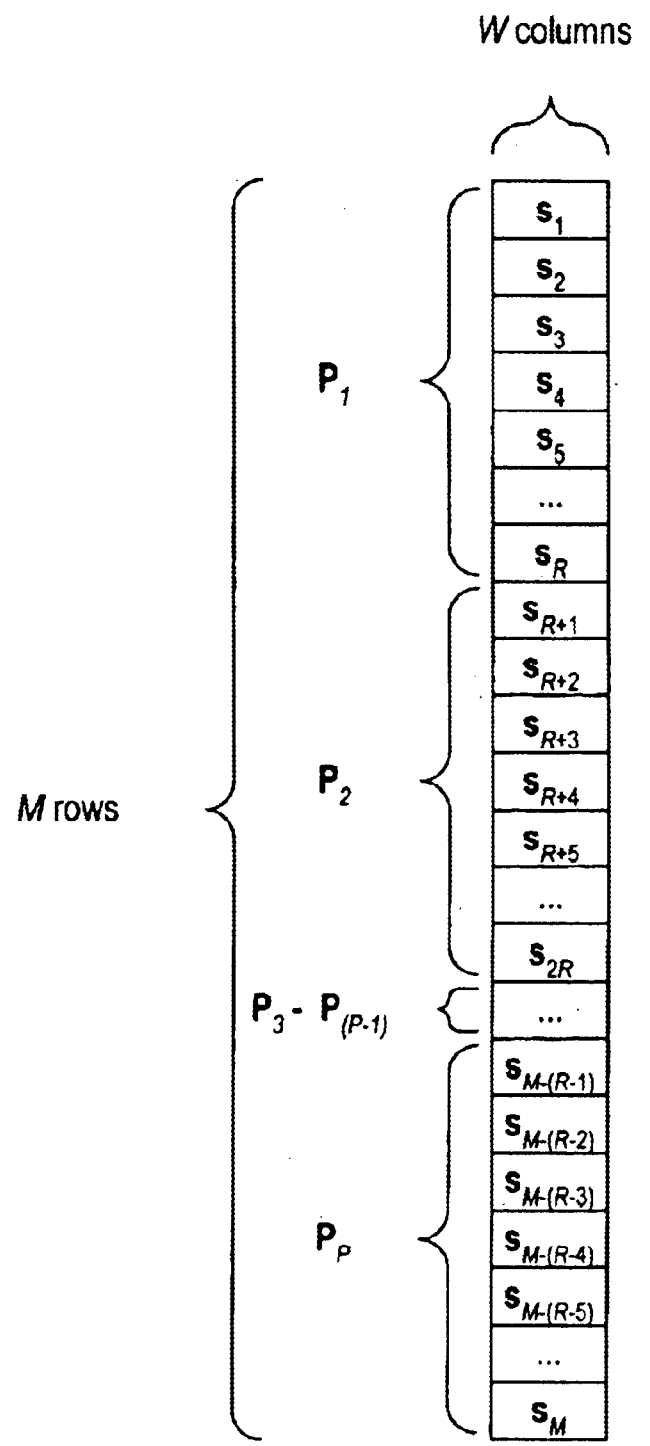
FIG. 12A depicts data samples $s_1 \ldots s_M$ of measurement M in a folded matrix X.
Figure 12C:
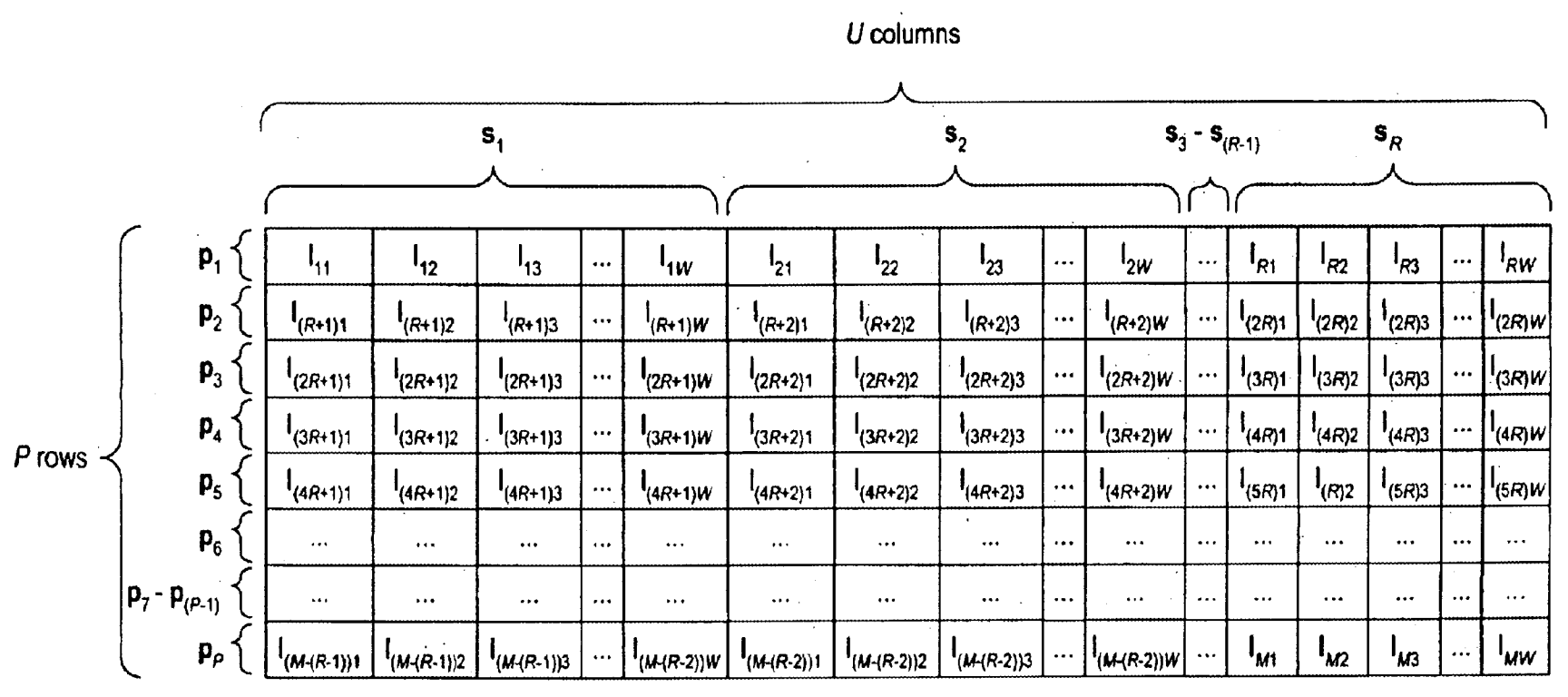

In the second way, a superior predictive model may be created from non-filtered, synchronously sampled periodic data by arranging the training data differently in the matrix X such that each of the rows holds data taken at a unique period. The data should be sampled synchronously with the period of the signal. In the measurement M, the spectra s, may be grouped by periods $P_j$, see FIG. 12A. For the first period, $P_1$=[$s_1; s_2; \ldots ; s_R$] where there are R spectra in a period. In general, $P_i$=[$s_{(i-1)R+1}; s_{(i-1)R+2}; \ldots ; s_{iR}$]. In this way, M=[$P_1; P_2; \ldots ; P_P$] where P is the number of periods in the measurement. Each $P_i$ may be rearranged into a row vector $p_i$ so that $p_1$=[$s_1, s_2, \ldots, s_R$] and $p_i$=[$s_{(i-1)R+1}, s_{(i-1)R+2}, \ldots, s_{iR}$]. Now the X matrix is rewritten, in the unfolded form, as X=[$p_1; p_2; \ldots; p_P$]. See FIG. 12B. In this arrangement, each row is a series of R spectra for one period of the signal. Each column in matrix X now has the samples that were measured at the same position in the period of the signal. Matrix X has P number of rows and U number of columns, where U=W·R. This matrix is described as unfolded and will be referred to as such hereinafter. Although not depicted in the figures, in most cases, the number of variables U is usually greater than the number P. FIG. 12C is an illustration of the unfolded matrix X which explicitly shows the intensity values $I_{ij}$.

Recall also that matrix X may be created from any type of measurement where the samples s, of measurement M comprise a plurality of measurements when the readings, $G_{tj}$, are taken simultaneously, where $s_t = \{G_{t1}, G_{2i2}, \ldots G_{iK}\}$. If readings $s_t$ are sampled synchronously, then the reading may be arranged such that matrix X is unfolded. Thus, superior results in identifying appropriate measurements for event detection using the PLS-DA algorithm of the present invention may be achieved by organizing the reading data in an unfolded matrix X in an identical manner as that described above for intensity values. Of course, a valid predictive model requires that the signal obtained from calibration data have some feature that correlates to the event to be detected using the predictive model.

In either arrangement, the measured spectra have a number of highly correlated measurements that describe the behavior of the process. The challenge is dealing with this large number of correlated variables. As mentioned above, the PCA algorithm is unsuitable for this task when the noise sources are large or the signal is small, which is often the case.

Discriminant Analysis is employed to divide samples into classes based on features of the samples and associates variables with the classes. Generally, the class matrix Y is composed of N rows of C-dimensional vectors, where C is the number of classes and N is the number of time samples in the problem (see FIG. 10). For a sample, or observation, there are several ways to assign discriminant variables to the classes. In the one way, the discriminant variable of the first class has the value of "1" if the sample is in the first class and is "0" if the sample is not in the first class. The discriminant variable of the second class has a value of "1" if the sample is in the second class, and "0" if it is not in the second class and so forth through the $C^{th}$ class. Thus, the $k^{th}$ component of the vector is 1 if the sample belongs to the $k^{th}$ class and 0 if it does not belongs to the $k^{th}$ class. In this case, the cut-off limit is 0.5. In the another way, the kth component of the vector is "1" if the sample belongs to the class k and "−1" otherwise. The cut-off value is "0" here. In another way, the discriminant variables may be given values so that the column vectors of matrix Y have a mean of zero.

Figure 13A:
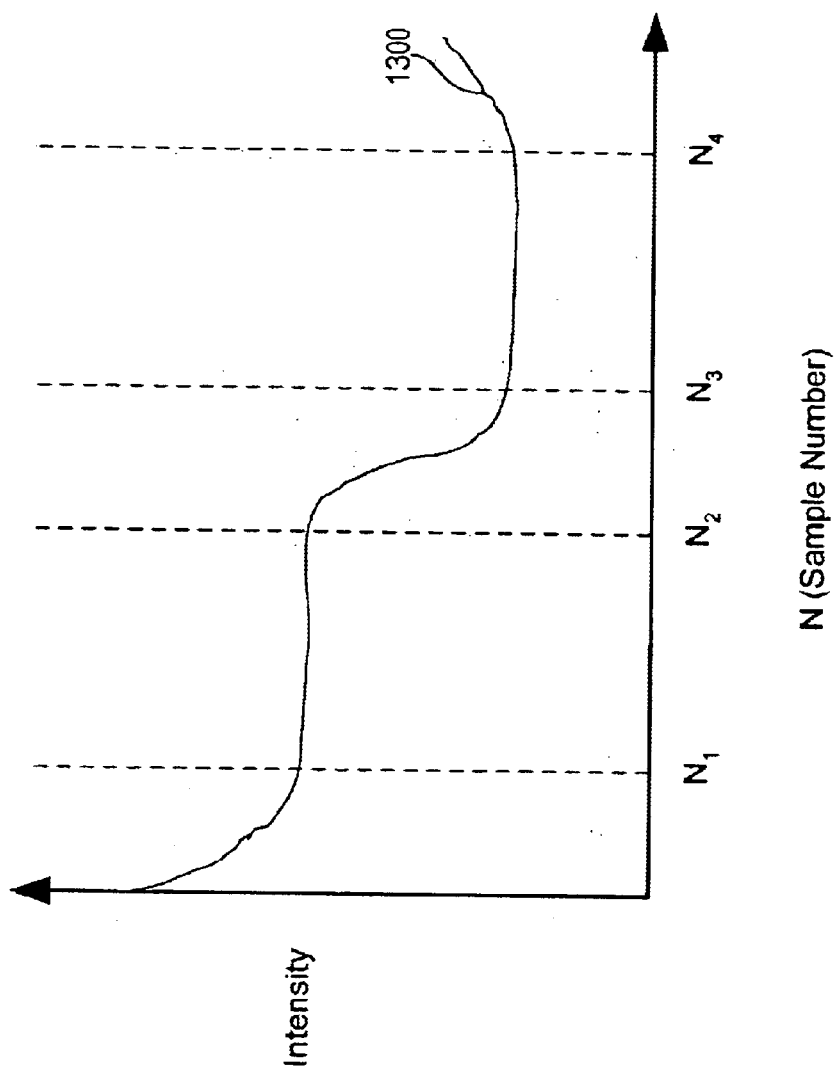
FIG. 13A is an illustration of endpoint signal 1300 for an etch, where the stable intensity values for the etch process can be clearly distinguished from other stable intensity values not in the class of stable values.
Figure 13B:
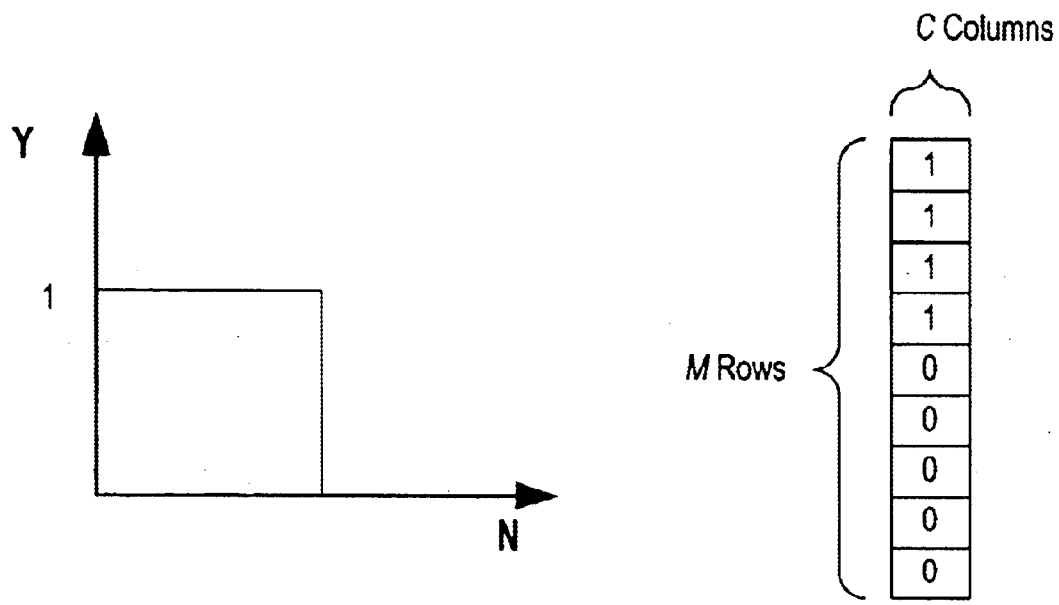
FIG. 13B shows a one-class response vector y having values that are selected for one class of high intensity values.
Figure 14B:
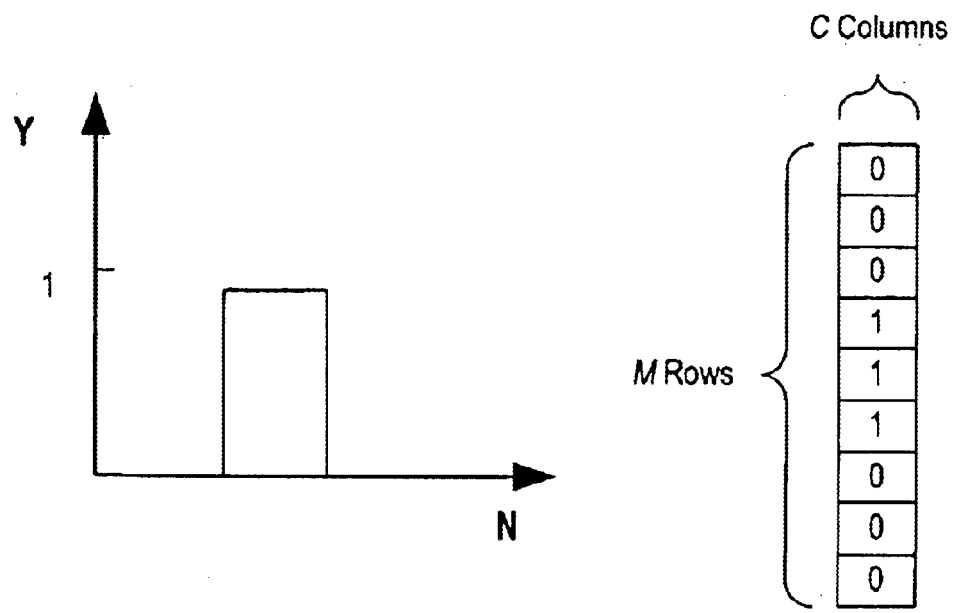
FIG. 14B shows a one-class response vector y having values that are selected for one class of derivative values.

The assignment of discriminant variables in the class matrix Y is better understood with reference to FIGS. 13A–C and FIGS. 14A–C. FIG. 13A is an illustration of endpoint signal 1300 for a wavelength for an etch where the stable intensity values for the etch process can be clearly distinguished from other stable intensity values not in the class of stable values, i.e. etch process intensity values. Samples for the depicted wavelength show higher intensity values in the etch region (samples $N_1$–$N_2$) and lower intensity values in the post-etch region (samples $N_3$–$N_4$). Other wavelengths may not show the exact character of signal 1300, but might instead show lower intensity values in the etch region and higher intensity values in the post-etch region. FIG. 14A is an illustration of derivative 1400 of the data for endpoint signal 1300. This shows low derivative values in the transition between the etch and post-etch regions (samples $N_2$–$N_3$) and higher derivative values in both the etch region (samples $N_1$–$N_2$) and post-etch region (samples $N_3$–$N_4$). A one-class matrix Y could be constructed by dividing the derivative data into classes based on the relative value of the derivative data in either case.

Figure 13C:
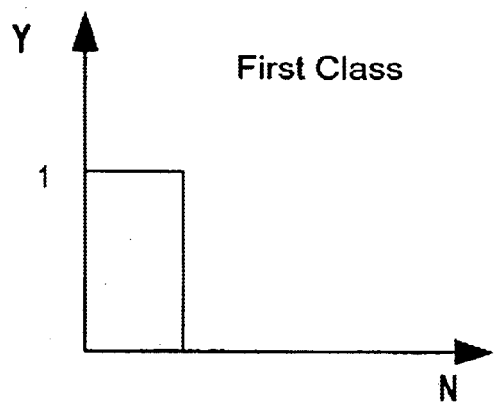
FIG. 13C shows a C-class response matrix Y having values that are selected for C classes of high intensity values.
Figure 13C:
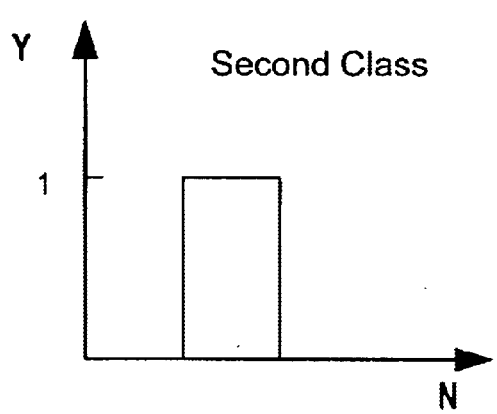
Figure 13C:
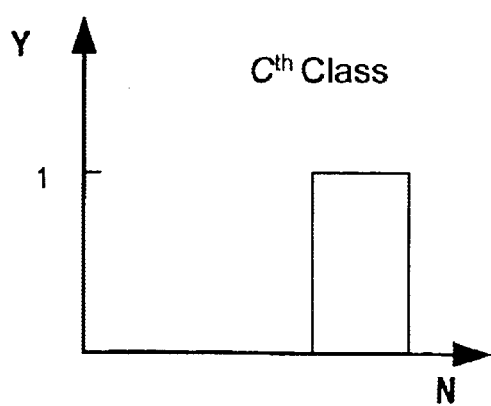
Figure 14C:
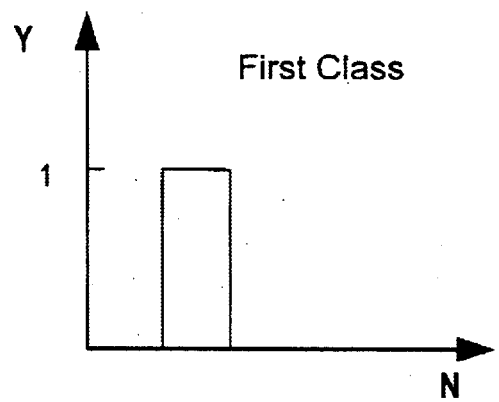
FIG. 14C shows a C-class response matrix Y for derivative values.
Figure 14C:
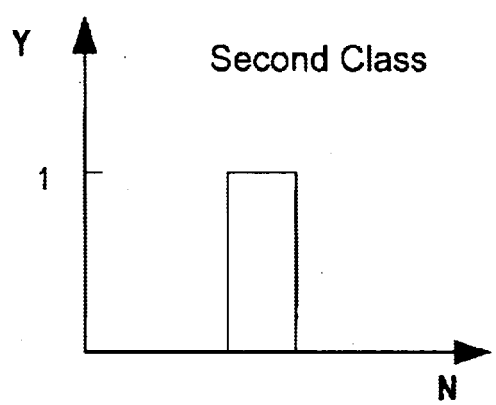
Figure 14C:
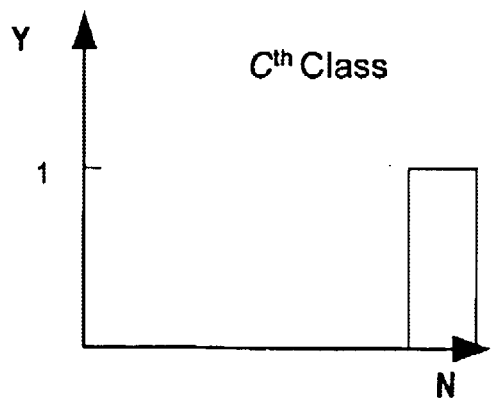
Figure 14C:
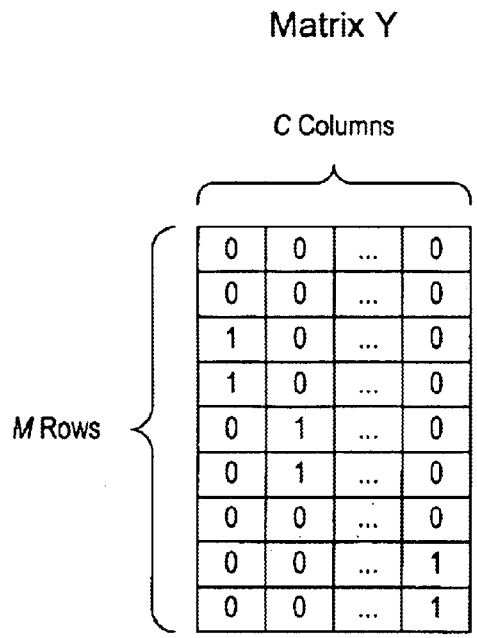

FIG. 13B shows one class of Y values that are selected for one class of high intensity values. With regard to signal 1300, this class represents the etch region. FIG. 14B shows one class of Y values that are selected for one class of low derivative values. With regard to derivative 1400, this class represents the transition region. The response matrix Y may be extended for C classes as illustrated in FIGS. 13C and 14C by adding column vectors for the additional classes. These new classes represent additional events, such as etch endpoints of other layers.

In any of the cases described above, when a predictor matrix X is created from the calibration data and a class matrix Y is constructed for the features in the samples, a regression matrix B is found by using PLS regression on the X and V matrices. In most cases that we observed, one latent variable is sufficient for the PLS regression to give good results. However, more than one latent variable can be used. The regression matrix B is then validated by comparing the resultant endpoint signal, that was produced from the inner product of a test matrix X and the regression matrix B, to a endpoint signal that is known to be appropriate for identifying the endpoint for the particular etch process. In practice, the entire calibration data set may be used as the test matrix X.

The ultimate goal is to obtain a stable model that gives reliable endpoint predictions. For one-class data, the response vector y is the endpoint signal. The vector $x_0$ may be a single measurement of a spectrum or it may be the unfolded data for a single magnet rotation. According to S. de Jong in SIMPLS, the usual expression for predicting new observations of the endpoint signal $y_0$ is:

$$y_0 = x_0 b \qquad (4)$$

Figure 15A:
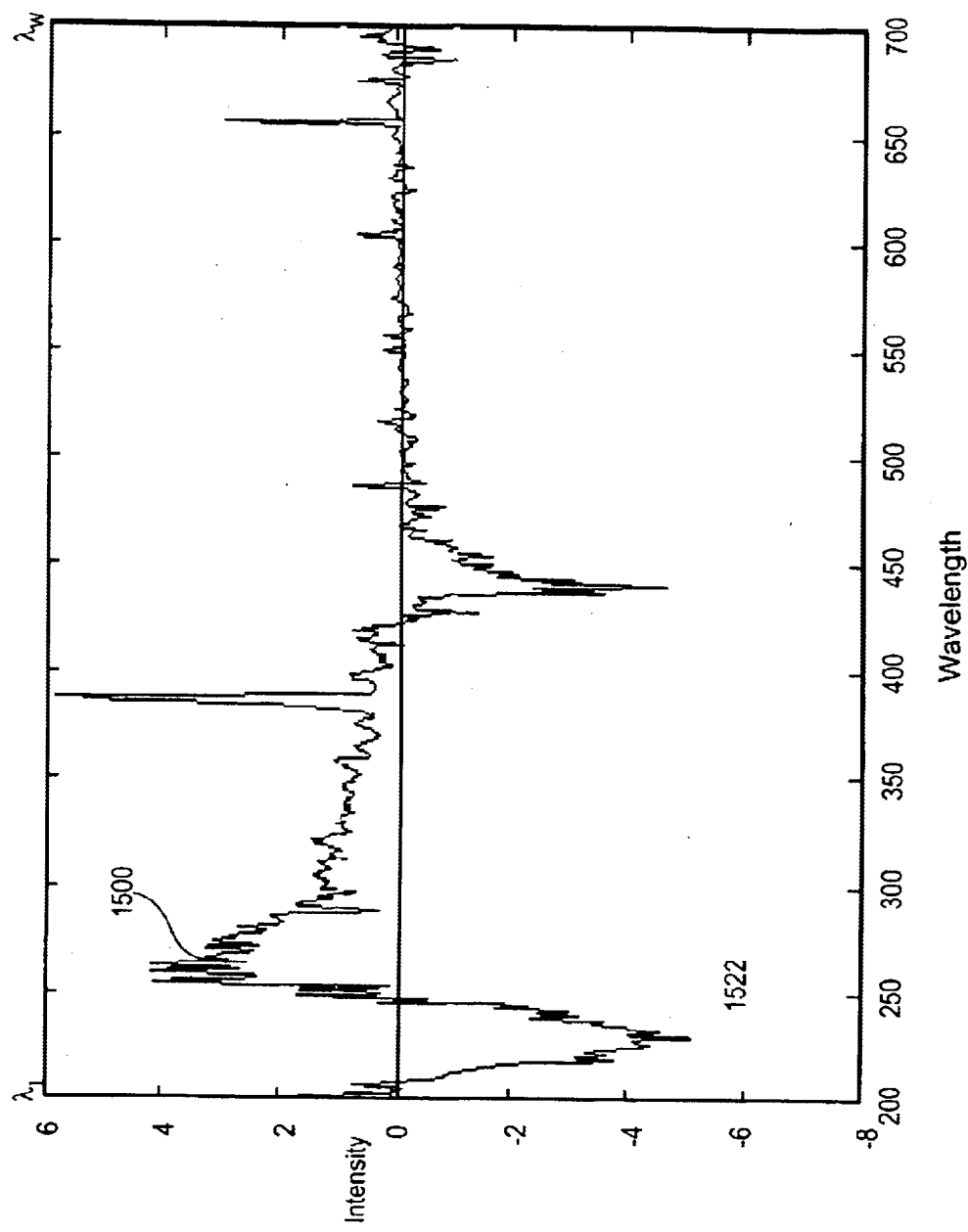
FIG. 15A is a diagram of exemplary b-vector 1500 having indices for wavelengths from 200 nm to 700 nm.

This is known as the inner product, or simply the IP method, for determining an endpoint signal $y_0$. The regression vector b was produced from calibration data for an etch process identical to that which generated the data in vector $x_0$. Therefore, the endpoint signal $y_0$ corresponds to the endpoint signal of the calibration data. A b-vector 1500 resulting from the regression of a predictor spectra matrix X and response y-block is illustrated in FIG. 15A. The b-vector 1500 has indices for wavelengths from 200 nm to 700 nm.

For synchronous signals, the b-vector obtained from calibration can be used to calculate an endpoint signal for each period. However, the endpoint signal at each sample time can also be calculated. The sampled data in X is collected for one period of data starting with the last sample and going back for one period. The b-vector is then changed by moving it's elements to correspond to the correct phase of the data samples in the x-vector. The phase of the b-vector must be the same as the samples in x-vector. This is done in the code for the endpoint algorithms that follow. An analogous calculation is done when B and X are matrices.

The following is code for implementing the IP method described by Equation (4) above for endpoint calculations.

```
function [Signal] = sig_ip(data_raw, perd, icol, cpos, b, wave)
ii_wave = wave.*2;
ii_wave = ii_wave-399;
data = data_raw(:,ii_wave);
Nsr = size(icol,2); % number of pixels in spectra that are processed
% create matrix bmat
% put spectra in b in rows for magnet positions that are in cpos
% put 0 in rows for magnet positions that are not included in cpos
bmat = zeros(perd,Nsr); % reserve space in memory
jj=1;
for ii=1:length(cpos)
     bmat(ii,:) = b(1,Nsr*(jj-1)+1:Nsr*jj);
     jj=jj+1
end
clear ii jj
% Apply filter bmat to data
Signal = zeros(size(data,1),1);
for ii = 1:size(data,1),
     if ii < perd
         Signal(ii) = 0.0;
     else
         SigTemp = 0;
         for jj = 0:(perd-1),
             Rmod = mod((ii-jj),perd); % signed remainder after division (ii-jj)/perd
             if Rmod ~= 0
                 SigTemp = SigTemp + data(ii-jj,:)*bmat(Rmod,:)';
             else
                 SigTemp = SigTemp + data(ii-jj,:)*bmat(perd,:)';
             end
         end
         Signal(ii) = SigTemp;
     end
end
return
```

Figure 15B:
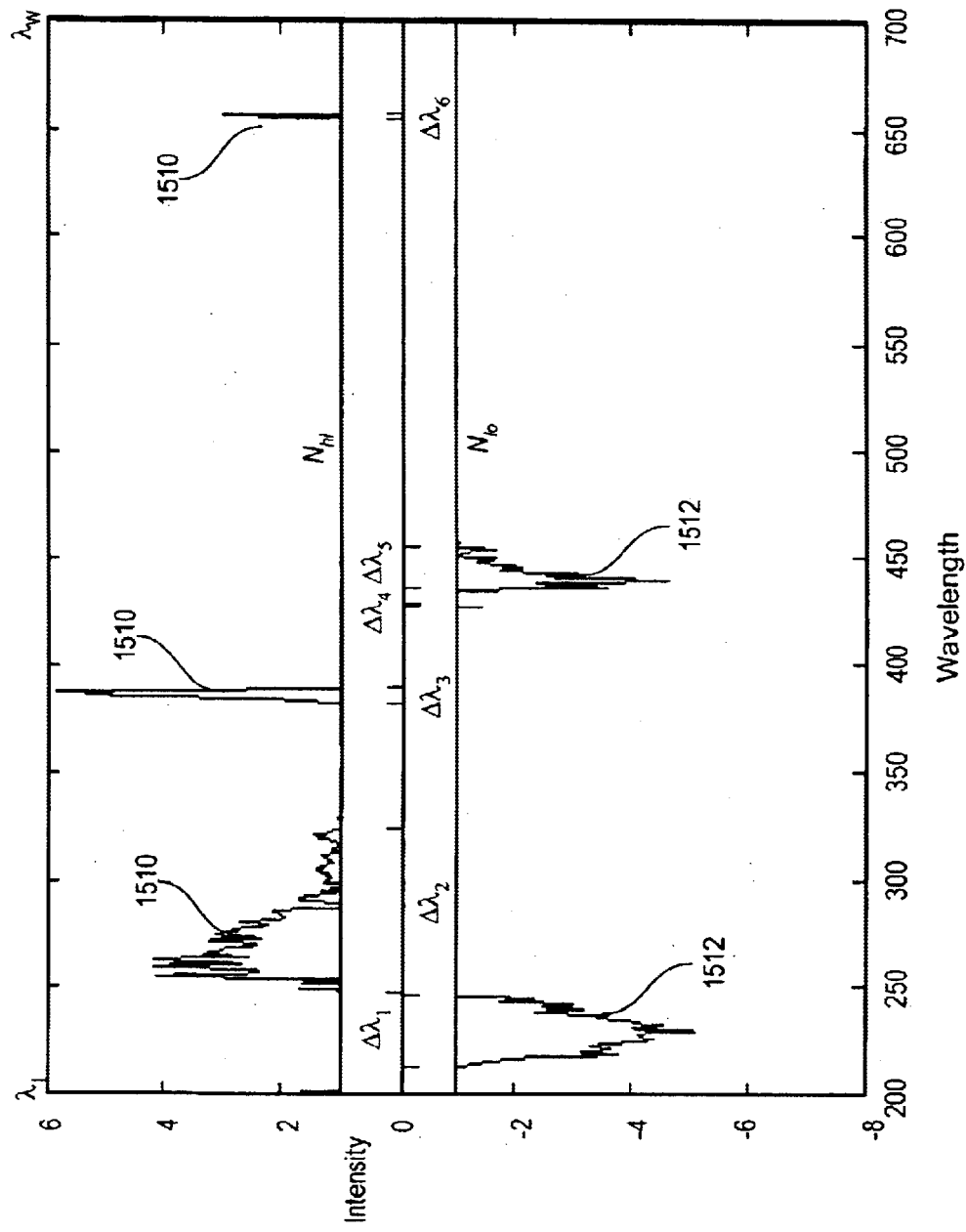
FIG. 15B is a diagram illustrating the $b_{hi}$ vector 1510 consisting of the components of b in the intervals $\Delta\lambda_2$, $\Delta\lambda_3$ and $\Delta\lambda_6$ that are above some cut-off limit, $N_{hi}$, and the $b_{lo}$ vector 1512 consisting of the components of b in the intervals $\Delta\lambda_1$, $\Delta\lambda_4$ and $\Delta\lambda_5$ that are below some cut-off limit, $N_{lo}$ of b-vector 1500.

For simple cases such as FIG. 13A and class vectors such as FIG. 13B, we interpret the positive values of b to correspond to wavelengths of intensites that decrease at endpoint and the negative values of b to correspond to wavelengths of intensities that increase at endpoint. The interpretation of b should be done with caution, and it is not necessary to have an explicit interpretation to use the method. A second expression for the endpoint signal $y_0$ is, $$y_0 = \frac{\sum_{i=iihi} x_{0_i} \cdot b_i}{\sum_{i=iilo} x_{0_i} \cdot b_i} \quad (5)$$

where iihi is a vector of the indices of the b-vector where the components of b are above some cut-off limit, $N_{hi}$, and iilo is a vector the indices where the components of b are below a second cut-off limit, $N_{lo}$. This is the sum of the inner products ratio method, or the IP-Ratio method, for determining an endpoint signal $y_0$. There is noise in any measurement system, so the regression vector b is subject to error. The cut-off limits eliminate some of this noise. Wavelengths where the components of b are greater than the positive cut-off limit $N_{hi}$ are kept and all others are set to zero in the $b_{hi}$ vector. Further, those wavelengths that are less than the negative cut-off $N_{lo}$ are similarly kept in the $b_{lo}$ vector. Also, by taking the ratio of the inner products, systematic drift is compensated to some extent and the signal is increased at endpoint since the numerator is increasing and the denominator is decreasing. FIG. 15B is a diagram illustrating the $b_{hi}$ vector 1510 consisting of the components of b-vector 1500, depicted in FIG. 15A, for wavelengths $\Delta\lambda_2$, $\Delta\lambda_3$ and $\Delta\lambda_6$ that are above some cut-off limit, $N_{hi}$, and the $b_{lo}$ vector 1512 consisting of the components of b-vector 1500 for wavelengths $\Delta\lambda_1$, $\Delta\lambda_4$ and $\Delta\lambda_5$ that are below some cut-off limit, $N_{lo}$. This second expression is not PLS-DA but is directed by the results of PLS-DA.

Below is code for implementing the IP Ratio method described by Equation (5) above for endpoint calculations.

```
function [Signal] = sig_ip_ratio(data_raw, perd, icol, cpos, b, wave)
% find indices of kept wavelengths
ii_wave = wave.*2;
ii_wave = ii_wave-399;
% select data that is kept in data preprocessing
data = data_raw(:,ii_wave);
Nsr = size(icol,2); % number of pixels in spectra that are processed
% create matrix bmat
% put spectra in b in rows for magnet positions that are in cpos
% put 0 in rows for magnet positions that are not included in cpos
bmat = zeros(perd,Nsr); % reserve space in memory
jj=1;
```

```
for ii=cpos
    bmat(ii,:) = b(1,Nsr*(jj-1)+1:Nsr*jj);
    jj=jj+1
end
clear ii jj
% create filter matrices MatLo & MatHi
MatLo = zeros(perd,Nsr); % reserve space in memory with zeros
MatHi = zeros(perd,Nsr); % reserve space in memory with zeros
for ii=cpos,
    MatLo(ii, find( bmat(ii,:)<0 )) = bmat(ii, find( bmat(ii,:)<0 ));
    MatHi(ii, find( bmat(ii,:)>0 )) = bmat(ii, find( bmat(ii,:)>0 ));
end
% Apply filter MatLo & MatHi to data
Signal = zeros(size(data,1),1);
for ii = 1:size(data,1),
    if ii < perd
        Signal(ii) = 0.0;
    else
        SigDen = 0;
        SigNum = 0;
        for jj = 0:(perd-1),
            Rmod = mod((ii-jj),perd); % signed remainder after division (ii-jj)/perd
            if Rmod == 0
                SigDen = SigDen + data(ii-jj,:)*MatLo(perd,:)';
                SigNum = SigNum + data(ii-jj,:)*MatHi(perd,:)';
            else
                SigDen = Sig Den + data(ii-jj,:)*MatLo(Rmod,:)';
                SigNum = SigNum + data(ii-jj,:)*MatHi(Rmod,:)';
            end
        end
        Signal(ii) = - SigNum/SigDen; % minus sign because denominator is negative
    end
end
return
```

A third method for determining an endpoint signal, the ratio of sums of the intensities or the Ratio method, is calculated as the ratio of the sum of intensities that increase to the sum of intensities that decrease:

$$y_0 = \frac{\sum_{i=iihi} x_{0_i}}{\sum_{i=iilo} x_{0_i}} \quad (6)$$

where iihi is a vector of the indices of the b-vector when the components of b are above some cut-off limit, $N_{hi}$, and iilo is a vector of the indices of the b-vector where the components of b are below a second cut-off limit, $N_{lo}$. This third method is not PLS-DA but is directed by the results of PLS-DA.

Below is code for implementing the Ratio method described by Equation (6) above for endpoint calculations

```
function [Signal] = sig_ratio(data_raw, perd, icol, cpos, b, Nsplo, Nsphi, wave)
% find indices of kept wavelengths
ii_wave = wave.*2;
ii_wave = ii_wave-399;
% select data that is kept in data preprocessing
data = data_raw(:,ii_wave);
Nsr = size(icol,2); % number of pixels in spectra that are processed
% create matrix bmat
% put spectra in b in rows for magnet positions that are in cpos
% put 0 in rows for magnet positions that are not included in cpos
bmat = zeros(perd,Nsr); % reserve space in memory
jj=1;
for ii=cpos
    bmat(ii,:) = b(1,Nsr*(jj-1)+1:Nsr*jj);
    jj=jj+1;
end
clear ii jj
% create filter matrices MatLo & MatHi
MatLo = zeros(perd,Nsr); % reserve space in memory with zeros
MatHi = zeros(perd,Nsr); % reserve space in memory with zeros
for ii=cpos,
    MatLo(ii, find( bmat(ii,:)<Nsplo )) = 1;
    MatHi(ii, find( bmat(ii,:)>Nsphi )) = 1;
```

-continued

```
end
% Apply filter MatLo & MatHi to data
Signal = zeros(size(data,1),1);
for ii = 1:size(data,1),
    if ii < perd
        Signal(ii) = 0.0;
    else
        SigDen = 0;
        SigNum = 0;
        for jj = 0:(perd-1),
            Rmod = mod((ii-jj),perd); % signed remainder after division (ii-jj)/perd
            if Rmod == 0
                SigDen = SigDen + data(ii-jj,:)*MatLo(perd,:)';
                SigNum = SigNum + data(ii-jj,:)*MatHi(perd,:)';
            else
                SigDen = SigDen + data(ii-jj,:)*MatLo(Rmod,:)';
                SigNum = SigNum + data(ii-jj,:)*MatHi(Rmod,:)';
            end
        end
        Signal(ii) = SigNum/SigDen;
    end
end
return
```

Figure 15C:
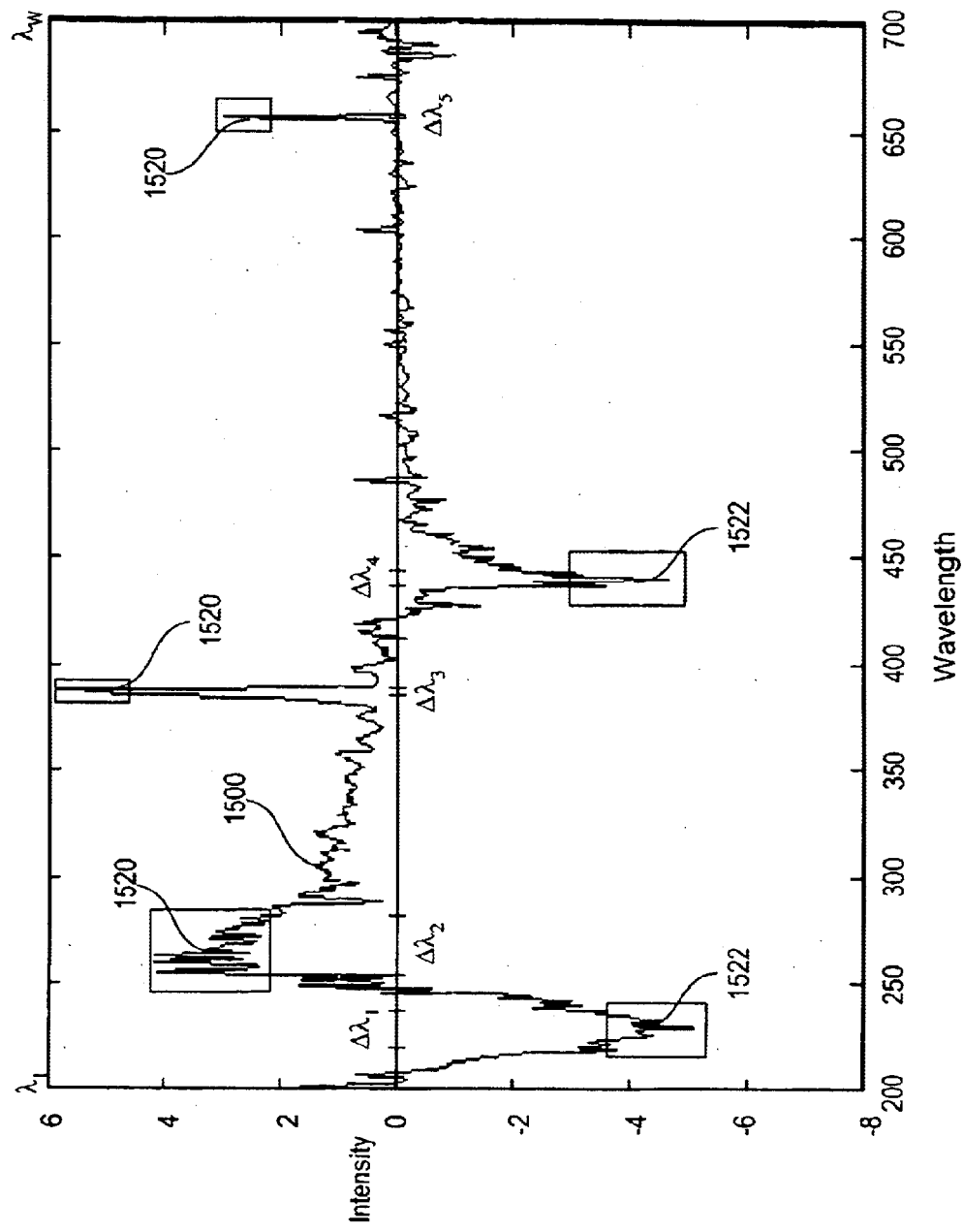
FIG. 15C is a diagram illustrating the $b_{hipeak}$ vector 1520 consisting of the components of b in the intervals $\Delta\lambda_2$, $\Delta\lambda_3$ and $\Delta\lambda_5$ that are manually selected from positive peaks of b-vector 1500 and the $b_{lopeak}$ vector 1522 consisting of the components of b in the intervals $\Delta\lambda_1$ and $\Delta\lambda_4$ that are manually selected from negative peaks of b-vector 1500.

A final method for determining an endpoint signal, the ratio of manually identified sums of the peak intensities or Peak-Ratio method, is calculated as the ratio of the sum of peak intensities that increase to the sum of peak intensities that decrease:

$$y_0 = \frac{\sum_{i=iipeakhi} x_{0_i}}{\sum_{i=iipeaklo} x_{0_i}} \quad (7)$$

where iipeakhi is a vector of the manually selected indices of the components of the b-vector which form some peak in the positive direction, those components of b are put in the $b_{hipeak}$ vector. Where iipeaklo is a vector of the manually selected indices of the components of the b-vector which form some peak in the negative direction, those components of b are put in the $b_{lopeak}$ vector. The Peak-Ratio method is an extension of the Ratio method, but because the Peak-Ratio method uses parts of the b-vector without regard to the magnitude of those parts, the cut-off limits vary from part to part, and therefore they must be manually identified on the b-vector. FIG. 15C is a diagram illustrating the $b_{hipeak}$ vector 1520 consisting of the components of b with the indices for wavelengths $\Delta\lambda_2$, $\Delta\lambda_3$ and $\Delta\lambda_5$ that are manually selected positive parts. The $b_{lopeak}$ vector 1522 consists of the components of b with the indices for wavelengths $\Delta\lambda_1$ and $\Delta\lambda_4$ that are manually selected negative parts of b-vector 1500 depicted in FIG. 15A. This last method is not PLS-DA but is directed by the results of PLS-DA.

Figure 16:
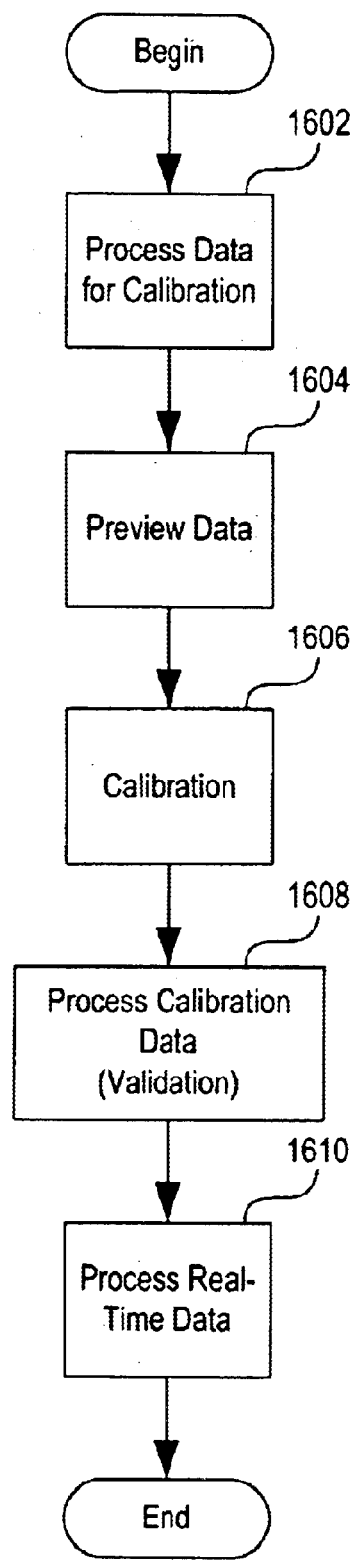
FIG. 16 is a high-level flowchart depicting a process that uses partial least squares discriminant analysis (PLS-DA) to create a predictive model of an etch process and to determine the endpoint of the process in accordance with an exemplary embodiment of the present invention.

FIG. 16 is a high-level flowchart depicting a process for using partial least squares discriminant analysis (PLS-DA) for creating a predictive model of an etch process and determining the endpoint of the process in accordance with an exemplary embodiment of the present invention. The process depicted in FIG. 16 illustrates only the general case which is applicable for any OES data set and will be expanded for the specific cases described in the embodiments below. The PLS-DA process of the present invention will be described in greater detail with specific regard to particular exemplary embodiments described below. Initially, the process begins by processing data for calibration (step 1602). In accordance with an exemplary embodiment of the present invention, the processing typically involves collecting optical emission spectroscopy (OES) data that is generated during the etch of a calibration wafer. Although it should be understood that the present process is equally adaptable for generating a predictive model for etch processes and determining events other than the endpoint of an etch process, i.e. types of data other than OES data may be used for calibration. However, in accordance with an exemplary embodiment of the present invention, OES sampling of etch processes for endpoint determinations will be described in detail.

The calibration OES data must have a large, unambiguous endpoint signal, and the data must accurately reflect the production process. An exemplary calibration wafer can be a production wafer with a large open area or a specially prepared wafer. In general, the larger the open area of the calibration wafer, the more sensitive the present method will be in detecting endpoint in production wafers with a small open area. Occasionally, the calibration wafers require special processing. Etching calibration wafers that have no resist on their surfaces, such as blanket wafers, gives spectra for a 100% open area and produces, in our experience, the most useful calibration data. Wafers with less than 100% open area can also be used. In general, it is important in the construction of a regression model that all the variations that will be present during the prediction are present in the calibration.

Additionally, the calibration wafers should have the same etch film over the same stop layer as the production wafers. Both films should be made of the same materials as the films in the production wafers and deposited in the same way. Significant differences in the chemical nature of the etch film or stop film will degrade or void the calibration. The films should be on a smooth, unpatterned wafer surface. However, a production wafer that has not been patterned may be used for a calibration wafer if the topology is smooth enough. Culled production wafers are often used for obtaining calibration data if they provide an endpoint signal. Both the etch layer and stop layer should be sufficiently thick to produce stable etching for a minimum of 30 seconds before endpoint and 30 seconds after endpoint. Additionally, the films should have uniformity across the wafer so that the etch film clears uniformly across the wafer surface. Finally, it is good practice to acquire at least two successful etches for each type of calibration wafer in order to check the raw calibration data sets against each other for unexpected anomalies.

With respect to the data itself, the calibration data collection should be stored using the identical data storage conditions as those used for storing the production data, i.e. using compatible software products using identical option parameter settings. Additionally, slight variations between physical components and/or the construction of the different etch chambers may alter the OES data. Therefore, calibration data should be taken with an etch tool identical to that which will be used in production. Additionally, the plasma chemistry should be the same in the calibration process as in the production process, and the process itself should be stable over time. If the data is periodic and the data is detected synchronously, then a minimum of four samples per period must be chosen to capture the variation of the signal. However, significantly more samples per period are often desirable to avoid regions where there are large amounts of noise.

It is expected that the OES data from the calibration wafer is arranged in a folded spectra matrix X, i.e. one row for each sample in the OES data. If not, a folded spectra matrix X can be created prior to creating the training data set.

Processing the OES data also includes removing deceptive or ambiguous data depending on whether the OES data is non-periodic or if periodic, whether it was sampled synchronously with the period of the signal or asynchronously. A derivative in time may be done for the spectra matrix X and saved separately if the analysis is to be performed on the derivative of the OES data set.

Next, the OES data is processed and an endpoint signal is previewed (step 1604). The PLS regression requires identifying the location of the endpoint transition. The previewed endpoint signal is used to identify samples (or sample times) associated with features to be classified. The processed data set of spectra matrix X can be viewed by PCA, a two-wavelength ratio, a moving average filter, or some other appropriate method. Generally, the previewed endpoint signal is taken from a wavelength in the OES data which has a well-defined endpoint. A typical endpoint signal is depicted in FIG. 13A as signal 1300.

The processed OES data is then calibrated using PLS-DA (step 1606). The training data set, which has OES data samples of the endpoint transition, is used in the X-block. For example, with reference to FIG. 13A, the transition region of the endpoint is located between two stable intensity regions that can be identified on endpoint signal 1300. These stable intensity regions correspond to OES data samples taken during the etch process and after the entire etch process has stopped, i.e. between $N_1$ and $N_2$ and between $N_3$ and $N_4$, from the preview endpoint signal.

Using the OES data samples taken between $N_1$ and $N_2$ and between $N_3$ and $N_4$ that were identified from the previewed endpoint signal, an X-block is created. A class matrix Y is also created that corresponds to the X-block. A regression b-vector is found by applying PLS to the X- and y-blocks (step 1606). The X-block is constructed from the processed OES data corresponding to samples taken between $N_1$ and $N_2$ and between $N_3$ and $N_4$. The X-block may be folded or unfolded depending on whether or not the OES data is periodic and sampled synchronously with its period. Synchronously sampled periodic OES data are arranged in the X-block one period of samples per row such that the X-block is unfolded. Non-periodic OES data and asynchronous periodic OES data are arranged in the X-block one sample per row such that it is folded. In addition to the X-block, a class matrix Y, the y-block, is created for classifying the features of the samples. The y-block is created by using binary partitioning. Generally, the class is defined as a region of stable higher or lower intensity values. A typical one-class vector y is shown in FIG. 13B, and FIG. 13C illustrates a typical C-class matrix Y.

In FIG. 16, the regression b-vector is then validated (step 1608). Validation takes the results of calibration and shows that it gives correct results. In this case, the data that was used for calibration is also used for validating the b-vector. So in the validation step, the raw calibration data is processed using the regression b-vector to give an endpoint signal. It is necessary to go through all the signal processing step, such as smoothing and elimination of saturated signals. This of course does not include the deletion of segments of the data. The method for calculating the endpoint signal $y_0$ should be the one that will be used for the real-time data. If endpoint signal $y_0$ does not compare favorably to the previewed endpoint signal, then the $N_1$, $N_2$, $N_3$ and $N_4$ samples were probably chosen incorrectly and should be chosen again, i.e. step 1606 is preformed again. If endpoint signal $y_0$ compares favorably to the previewed endpoint signal, then the regression vector b can be relied on for processing real-time data using one of the IP, IP-Ratio, Ratio or Peak Ratio method (step 1610).

The present process will now be described for the various specific cases, e.g. non-periodic signals, periodic signals sampled synchronously with the period of the signal (synchronous data) and periodic signals not sampled synchronously with the period of the signal (non-synchronous data).

NON-PERIODIC SIGNAL DATA

One-Class PLS-DA on OES Data

In accordance with one exemplary embodiment of the present invention, a predictive model of the endpoint of etch processes using Partial Least Squares Discriminant Analysis (PLS-DA) is created using data from non-periodic signals. By definition, non-periodic signals cannot be sampled synchronously because they have no repeating period. The process will be described with reference to the high-level flowchart depicted in FIG. 16 and described above. Deviations from the general case for the specific embodiments will be emphasized in the description below. The process begins by collecting raw OES data from a calibration wafer for a particular etch process and processing that data (step 1602). Generally, the OES data is arranged in a folded spectra matrix X with one sample per row.

Figure 17:
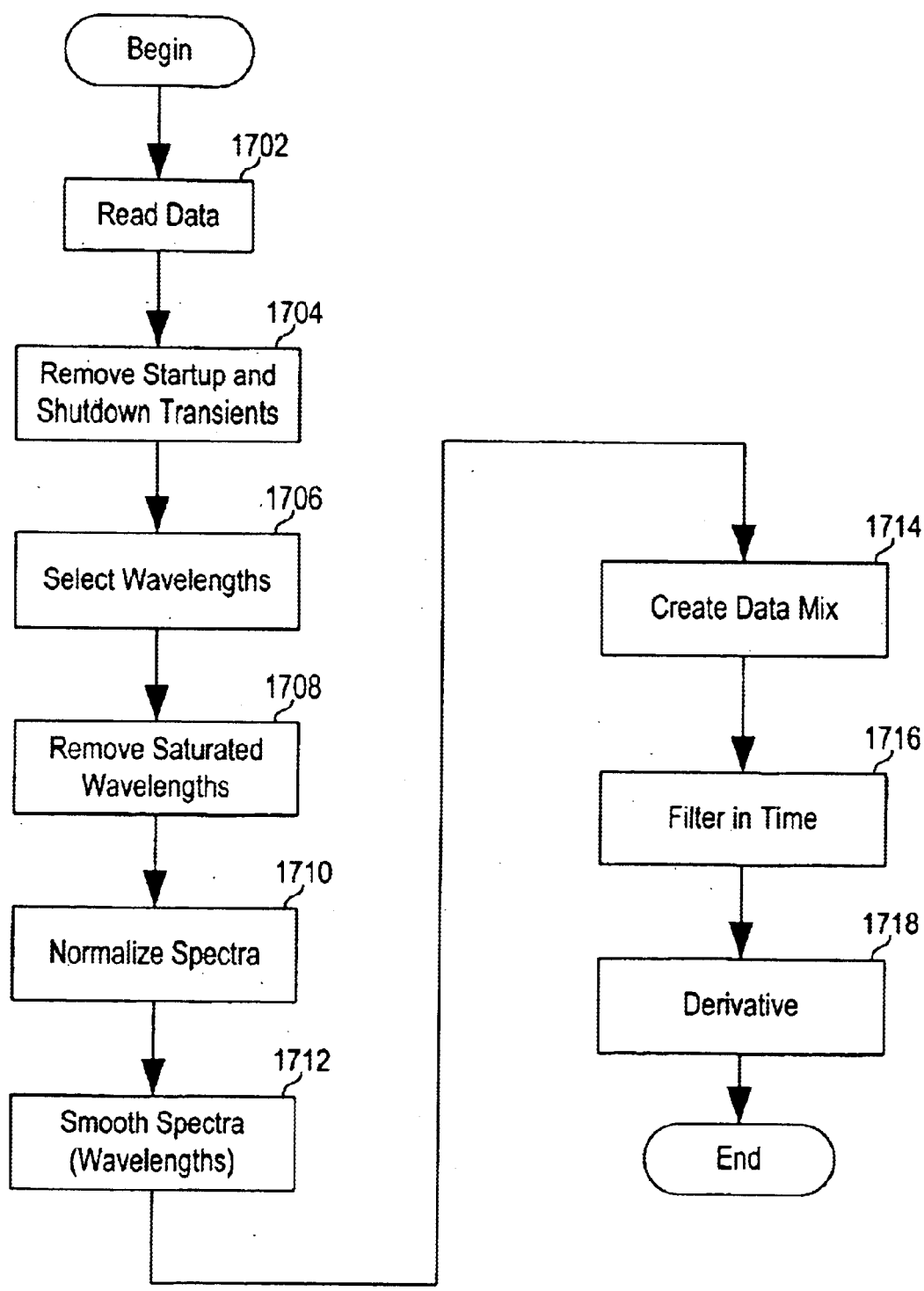
FIG. 17 is a detailed flowchart depicting a process for processing the OES data from the calibration wafer in accordance with an exemplary embodiment of the present invention.

FIG. 17 is a detailed flowchart of a process for processing the OES data from the calibration wafer in accordance with an exemplary embodiment of the present invention. The process of FIG. 17 is an expanded description of the process step illustrated by step 1602 in FIG. 16. Calibration begins by loading data from an appropriate calibration wafer from storage (step 1702). The data may be on a convenient storage medium, such as optical media(Compact Disk (CD), Digital Video Disk (DVD), etc.), magnetic media(hard drive, tape disk, etc.), or any other media capable of holding the necessary amount of data. Next, start-up and shut-down transients are removed from the data (step 1704). Wavelength regions are selected with desirable endpoint transition quality, such as sharpness (step 1706), and saturated wavelengths are wholly removed (step 1708). Next, the vectors of the spectra intensities, which are the rows of the spectra matrix X, are normalized to have a length of one (step 1710) and the additional smoothing of the data in wavelength dimension may be provided (step 1712). If, at this point, the processed data is not arranged in a folded spectra matrix X, the spectra matrix X is created (step 1714). If desired, Savitsky-Golay smoothing is applied on the time axis to obtain smoother endpoint curves (step 1716). Finally, a derivative in time is done on spectra matrix X if the analysis using the derivative is to be performed (step 1718).

Returning to the process depicted in FIG. 16, an endpoint signal is previewed from the processed spectra matrix X using dynamic PCA, a two-wavelength ratio, a moving average filter, or some other appropriate method (step 1604). A typical endpoint plot is shown as endpoint signal 1300 in FIG. 13A. The location of an endpoint transition is necessary for PLS regression and is selected based on the location of regions of stable intensity values on the previewed endpoint plot. A single class of intensity values is identified for the etch process. This class corresponds to one of the regions of stable intensity values and may have higher or lower intensity values than the other region of stable intensity values. The second region is attributable to the post-etch process. The sample numbers $N_1$ and $N_2$ are chosen to locate the stable region before endpoint and to exclude the start-up transient and the transition region. The sample numbers $N_3$ and $N_4$ are chosen to locate the stable region after endpoint and to exclude the transition region and the shut-down transient. By default, a region of unstable intensity values is identified as occurring between the two stable regions which corresponds to the transition region, i.e. between the $N_2$ sample and the $N_3$ sample. The endpoint transition region is shown as the region of endpoint 1300 where the intensity values are changing at endpoint between samples $N_2$ and $N_3$.

Figure 18:
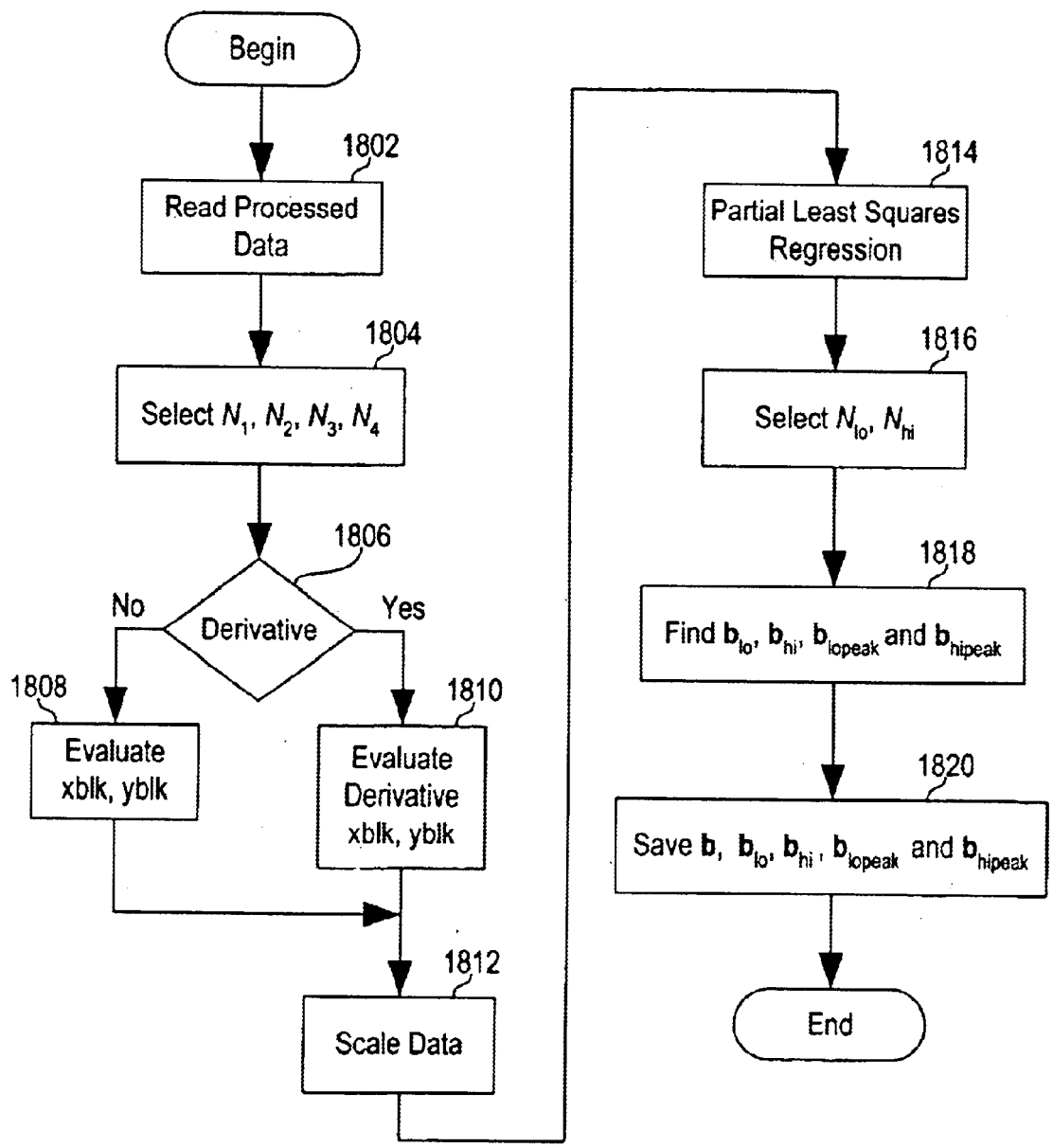
FIG. 18 is a detailed flowchart depicting a process for creating the X-block and y-block and using PLS regression to find a b-vector in accordance with an exemplary embodiment of the present invention.

The processed OES data is then calibrated using the PLS-DA process (step 1606). FIG. 18 is a detailed flow chart depicting a process for creating the X-block and y-block and using PLS regression to find a b-vector in accordance with an exemplary embodiment of the present invention. The process of FIG. 18 is an expanded description of the calibration process step illustrated by step 1606 in FIG. 16. The calibration process begins by reading the processed data in spectra matrix X (step 1802). Sample numbers $N_1$, $N_2$, $N_3$ and $N_4$ are picked from a previewed endpoint plot, such as endpoint signal 1300 as shown in FIG. 13A (step 1804). Sample numbers $N_1$ and $N_2$ are selected from the stable region before endpoint and sample numbers $N_3$ and $N_4$ are selected from the stable region after the endpoint.

The present PSL-DA algorithm is extremely flexible enabling a b-vector to be regressed from either the processed OES data in the spectra matrix X or the derivative with respect to time of the processed OES data. This particular embodiment is concerned with the processed OES data (step 1806). The X- and y-blocks are then created for the processed non-periodic OES data in the spectra matrix X (step 1808). A folded X-block is created from data located in the regions of stable intensity values, e.g. between sample numbers $N_1$ and $N_2$ and between sample numbers $N_3$ and $N_4$, having one OES sample per row. The y-block is then created for one class of stable intensity values using binary partitioning. Recall that the X-block was created from OES samples corresponding to two regions of stable intensity values on the previewed endpoint plot. Thus, with regard to one-class PLS-DA processing of the data in spectra matrix X, either the etch region or the post-etch region could be represented with a discriminate variable of "1" in the y-block. A convention for assigning discriminate values to the classes should be chosen prior to creating the y-block. Therefore, with respect to the one-class embodiment described herein, the etch region will be assigned a discriminate variable of "1." Regions other than the etch region will be assigned a discriminate variable of "0." Thus, a y-block is created using binary partitioning such that a discriminate variable value of "1" is assigned to the region for the etch process, corresponding to the $N_1$ to $N_2$ samples, and a discriminate value of "0" to all intensity values not in the class, corresponding to the $N_3$ to $N_4$ samples.

The data in the X-block and the y-block are scaled, typically mean centered, (step 1812) and the PLS regression is then performed on the X- and y-blocks resulting in a b-vector (step 1814). Next, $N_{lo}$ and $N_{hi}$ are selected for the b-vector (step 1816) and a $b_{lo}$ vector is found by limiting OES intensity values to less than $N_{lo}$ and $b_{hi}$ vector by limiting OES intensity values to greater than $N_{hi}$. Additionally, a $b_{hipeak}$ vector can be selected in 1706 by manually selecting indices of the b-vector which form some positive peak(s) and a $b_{lopeak}$ vector by manually selecting indices of the b-vector which form some negative peak(s). Each of the b, $b_{lo}$, $b_{hi}$, $b_{lopeak}$ and $b_{hipeak}$ vectors that are found in step 1818 are then saved for use in processing real-time OES data for endpoint detection (step 1820).

Returning now to FIG. 16, the regression b-vector is then validated (step 1608). If the endpoint signal $y_0$ produced from the inner product of the b-vector and the spectra matrix X differs in appearance from the previewed endpoint plot, then the locations of $N_1$, $N_2$, $N_3$ and $N_4$ samples were probably chosen incorrectly and should be chosen again and reprocessed from step 1606. If endpoint signal $y_0$ compares favorably to the previewed endpoint signal, then any of the b, $b_{lo}$, $b_{hi}$, $b_{lopeak}$ and $b_{hipeak}$ vectors can be relied upon for processing real-time non-periodic OES data using the IP, IP-Ratio, Ratio or Peak Ratio method (step 1610).

One-Class PLS-DA on the Derivative of Non-Periodic OES Data

In accordance with one exemplary embodiment of the present invention, a predictive model of the endpoint of etch processes using Partial Least Squares Discriminant Analysis (PLS-DA) is created using derivatives of non-periodic OES data. Using the derivative has an advantage over using OES data in that wavelengths that have a faster transition at endpoint are preferentially selected over others. The present process is essentially identical to that described above with the exception of the creation of the X- and y-blocks. Instead of using processed non-periodic OES data in the spectra matrix X as in the prior embodiment, here the time derivative of the processed OES data in the spectra matrix X is used. Therefore, a derivative in time must be taken on the processed OES data contained in spectra matrix X, if not already prepared in step 1718 of the process depicting in FIG. 17 above. The X- and y-blocks are then created using the derivative data in accordance with step 1810 of the expanded calibration process depicted in FIG. 18. Since the PLS regression is now to be performed on the derivatives of the OES data, the class must then represent some evolving or changing feature on the previewed endpoint plot. Clearly, the only feature apparent on a plot of the derivative values is the transition region (see again FIG. 14A). Therefore, derivative data from all sample numbers between $N_1$ and $N_4$ are arranged one sample per row to create a folded X-block. The y-block is then created for one class of unstable or evolving intensity values using binary partitioning. Since the class is now the transition region, a discriminate variable of "1" is assigned to the transition region in the y-block and a discriminate variable of "0" elsewhere. The X- and y-blocks can be regressed using PLS and validated identically to that described above for raw OES data. The resulting b, $b_{lo}$, $b_{hi}$, $b_{lopeak}$ and $b_{hipeak}$ vectors can be relied upon for processing real-time non-periodic OES data using the IP, IP-Ratio, Ratio or Peak Ratio method.

Although the above-described method for using Partial Least Squares Discriminant Analysis on derivatives of OES data was described with respect to the one-class case, it is equally applicable to a C-class case. Additionally, the above-described method for using Partial Least Squares Discriminant Analysis on derivatives of OES data is applicable to periodic OES data as well as non-periodic OES data, regardless of whether or not the periodic data was synchronously sampled. The C-class case and cases for handling periodic signals are described below.

C-Class PLS-DA on Non-Periodic OES Data

In accordance with one exemplary embodiment of the present invention, a predictive model of the C endpoints of etch processes using Partial Least Squares Discriminant Analysis (PLS-DA) is created using data from non-periodic signals. The present process is similar to that described above for the one-class case, but involves identifying transition regions associated with multiple endpoints.

When one layer is etched away, the etch process will erode the next layer and so on until the $C^{th}$ etch layer is etched away. Therefore, the calibration OES data must have C unambiguous endpoint transitions that accurately reflect all endpoints. The OES data may be arranged in a folded spectra matrix X and processed according to FIG. 17 above.

C transition regions associated with the C endpoints must be located on the previewed endpoint signal. Wavelength regions for each of the C endpoints must be selected with desirable endpoint transitions quality for the respective endpoints in step 1706. To preview an endpoint plot for picking the 2C+1 samples that define the C transition regions, a single endpoint plot may be produced from wavelength segments using dynamic PCA, a two-wavelength ratio, a moving average filter, or some other appropriate method (step 1604). Alternatively, C separate wavelengths may be selected, one for each of the C endpoints, each with desirable endpoint transitions quality for a respective endpoint.

Regardless of how the endpoints are previewed, the locations of the C transition regions must be selected as required by step 1804 in the expanded calibration process depicted in FIG. 18. The method for locating these regions is an extension of the one-class case. C+1 regions of stable intensity values are located on the previewed endpoint plot having C transition regions therebetween. The first region of stable intensity values (either highest or lowest values) is located before a first transition region of evolving intensity values which corresponds to an etch or post-etch region, e.g. between the $N_1$ sample and the $N_2$ samples. Next, a region of stable intensity values (either increasingly higher or decreasingly lower intensity values than the first stable region) are located between two transition regions of evolving intensity values which correspond to etch/post-etch region(s), e.g. between each of the $N_3$ and $N_4$ samples through the $N_{2C-1}$ and $N_{2C}$ samples. A last region (the $(C+1)^{th}$ region) of stable intensity values (either higher or lower intensity values than the highest or lowest intensity values for the (C-1) stable regions) is located after the $C^{th}$ transition region of evolving intensity values and corresponds to either the etch or post-etch region, e.g. between the $N_{2C+1}$ sample and the $N_{2C+2}$ sample. Lastly, C regions of evolving intensity values are located between each of the $N_2$ and $N_3$ samples through the $N_{2C}$ and $N_{2C+1}$ samples.

Next, the X- and Y-blocks are created in accordance with step 1808 of the expanded calibration process depicted in FIG. 18. The X-block is created from OES samples in the spectra matrix X between each of the $N_1$ to $N_2$ samples through the $N_{2C+1}$ to $N_{2C+2}$ samples. Therefore, the data in the X-block excludes OES data in the transition regions, i.e. between each of the $N_2$ and $N_3$ samples through the $N_{2C}$ and $N_{2C+1}$ samples. The data is arranged one sample per row in a folded X-block arrangement. The Y-block is then created by using binary partitioning. For each column in the Y-block, one assigns a discriminate variable value of "1" to the region of stable intensity values associated with the etch region for the particular etch being classified by that column, and a discriminate value of "0" everywhere else. An exemplary C-class Y-block is depicted in FIG. 13C.

The data in the X-block is scaled (step 1812) and the X- and Y-blocks are regressed using PLS regression resulting in a regression B matrix (step 1814). Note here that because the Y-block is a C column matrix, the regression B matrix also has C columns or C separate b-vectors, one for each endpoint. $N_{lo}$ and $N_{hi}$ are then selected for each b-vector (step 1816) and a $b_{lo}$ vector is determined for each b-vector by limiting OES intensity values to less than $N_{lo}$ and $b_{hi}$ vector by limiting OES intensity values to greater than $N_{hi}$. Additionally, a $b_{hipeak}$ vector may be found for each b-vector by manually selecting indices of that b-vector which forms some positive peak(s) and a corresponding $b_{lopeak}$ vector by manually selecting indices of the b-vector which form some negative peak(s). Each of the b, $b_{lo}$, $b_{hi}$, $b_{lopeak}$ and $b_{hipeak}$ vectors associated with each of the b-vectors, are then saved for use in processing real-time OES data for endpoint detection (step 1820).

The regression B matrix is then validated by obtaining an endpoint signal $y_0$ from the inner product of the regression b-vector and a vector $x_0$ (step 1608). If the endpoint signals $y_0$ for each etch transition endpoint produced from the inner product of the b-vector and the spectra matrix X differs in appearance from the previewed endpoint plots, then the locations of $N_1$ to $N_{2C+1}$ samples were probably chosen incorrectly and should be chosen again and reprocessed in step 1606. If the endpoint signals compare favorably to the previewed endpoint signal, then the regression matrix B can be relied on for processing real-time data using one of the IP, IP-Ratio, Ratio or Peak Ratio method for determining the respective C endpoints (step 1610).

Although the above-described method for using Partial Least Squares Discriminant Analysis of OES data was described with respect to the non-periodic data, it is applicable to periodic OES data, regardless of whether or not the periodic data was synchronously sampled. Cases for handling periodic signals are described below.

PERIODIC SIGNAL DATA

One-Class PLS-DA on Asynchronous OES Data

In accordance with one exemplary embodiment of the present invention, a predictive model of the endpoint of etch processes using Partial Least Squares Discriminant Analysis (PLS-DA) is created using non-synchronously sampled data from periodic signals. In this case, the signal has a repeating periodic component, but the data has not been sampled synchronously with the period. In this case, the periodic signal will appear as a noise on a plot of an endpoint signal, thereby masking the locations of regions that are necessary for PLS regression. However, the PLS-DA analysis of asynchronous OES data is exactly the same as non-periodic OES data described above, except that the spectra matrix X is filtered using an appropriate method to remove the noise (actually the periodic component) from the OES data. The process then proceeds as described above with respect to FIGS. 16–18 described above. Of course, because the b-vector was created from filtered OES data from the sample wafer, the real-time process OES data must be likewise filtered.

In accordance with another exemplary embodiment of the present invention, the b-vector may be created from unfiltered asynchronous OES data in exactly the same manner as described above for non-periodic OES data. The previewed endpoint plot must be filtered to remove the periodic component from the endpoint signal in order to select $N_1$, $N_2$, $N_3$ and $N_4$. The b-vector is validated by filtering the response vector $y_0$ (actual the endpoint signal) with the same filter to remove the periodic component for comparison with the previewed endpoint signal. Then, during real-time processing using one of the IP, IP-Ratio, Ratio or Peak Ratio methods, the resultant values of $y_0$ are filtered with the same filter to remove the periodic component and the endpoint chosen from the filtered real-time endpoint.

One-Class PLS-DA on Synchronous Periodic OES Data

In accordance with one exemplary embodiment of the present invention, a predictive model of the endpoint of etch processes using Partial Least Squares Discriminant Analysis (PLS-DA) is created using data from periodic signals which are sampled synchronously with the period of the signal. Essentially, the present process extends the method for one-class PLS-DA analysis of non-periodic OES data by processing OES samples with respect to their position in the period of the signal and then arranging the processed periodic OES data in an unfolded spectra matrix X and an unfolded X-block rather than in folded matrices as for non-periodic OES data.

The present process will be described with respect to the general case which is applicable for any OES data set as depicted in FIG. 16 and supplemented by flow charts depicting expansions of the general case that are necessary for understanding PLS-DA analysis of synchronously detected periodic OES data. The process begins by collecting raw OES data from a calibration wafer for a particular etch process and processing that data (step 1602). Generally, the OES data from the calibration wafer is arranged in a folded spectra matrix X with one sample per row for processing.

FIG. 15D is a diagram of an exemplary b-vector 1560 which is derived from synchronously sampled periodic OES data in accordance with an exemplary embodiment of the present invention. b-vector 1560 contains a wavelength component corresponding to every wavelength in each spectrum in a period. Since the period corresponds to a revolution of a magnet housing on a magnetically enhanced etcher, the samples correspond to 28 positions on the housing where the samples were taken. b-vector 1560 may be thought of as 28 separate b-vectors, one b-vector for each of the 28 sample positions on the housing, that are sequentially combined into a single b-vector. Therefore, vector 1560 contains a wavelength component for every wavelength in the sampled spectrum at each of the 28 sample positions. Of course, b-vector 1560 is exemplary and the actual number of wavelength components for a b-vector will depend on the actual number of magnet positions on the etcher and on the number of discrete wavelengths in the spectrum.

Figure 19:
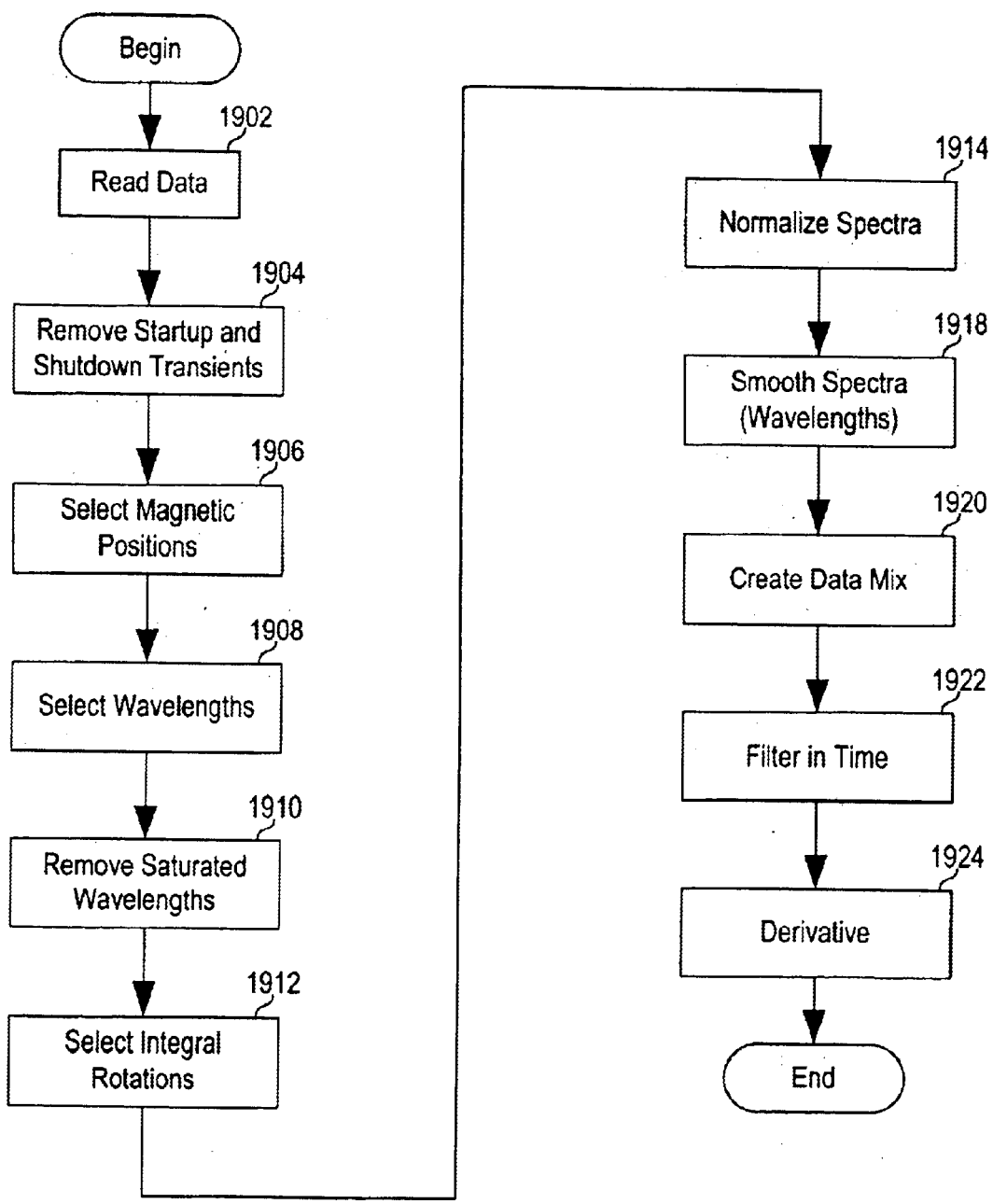
FIG. 19 is a flowchart depicting an expanded process for processing synchronously detected, periodic OES data from the calibration wafer in accordance with an exemplary embodiment of the present invention.

FIG. 19 is a flowchart depicting an expanded process for processing synchronously detected periodic OES data from the calibration wafer in accordance with an exemplary embodiment of the present invention. The process of FIG. 19 is an expanded description of the process step illustrated by step 1602 in FIG. 16, and is similar to that described by the method for processing data for calibration depicted in FIG. 17, but now includes processing steps for samples with respect to their position in the period of the signal. Calibration of the data from the calibration wafer begins by loading data from an appropriate calibration wafer from storage (step 1902). Start-up and shut-down transients are first removed from the data (step 1904) and data positions within a period are examined for large or anomalous noise. With respect to magnetically-enhanced etch processes, this noise may be associated with the magnetic positions that created the noise. The data samples associated with those positions should be removed from the data (step 1906). Wavelength regions are selected with desirable endpoint transition quality, such as sharpness (step 1908) and saturated wavelengths are wholly removed (step 1910).

Next, the data set is rounded to an integral number of rotations by removing data corresponding to partial rotations at the beginning and end of the etch (step 1912). Only data from complete periods are used in the spectra matrix X. The vectors of the spectra intensities can be normalized to have a length of one if desired (step 1914) and the additional smoothing of the data in the wavelength dimension can be done (step 1918).

An unfolded spectra matrix X is then created from the processed OES data (step 1920). Each period of sample data in the folded spectra matrix X is unfolded to a single row vector by placing sequentially each row of spectra for a period to the right of the first creating a row vector of processed OES data. For example, if the data for a period $P_t$ is a 12 by 1201 matrix, then $P_t$ is unfolded to a 1 by 14412 row vector. Data from subsequent periods in the spectra matrix X are placed below this row vector. The unfolding will remove variance due to the periodicity. If desired, Savitsky-Golay smoothing is applied on the time axis to obtain smoother endpoint curves (step 1922). Finally, a derivative in time is done on spectra matrix X if the analysis using the derivative is to be performed (step 1924).

Returning to the process depicted in FIG. 16, an endpoint signal is previewed from the processed data in spectra matrix X using dynamic PCA, a two-wavelength ratio, a moving average filter, or some other appropriate method (step 1604) (shown as endpoint signal 1300 in FIG. 13A). The location of an endpoint transition is identified for PLS regression based on the location of regions of stable intensity values in the previewed endpoint plot similar to that described above. Samples $N_1$, $N_2$, $N_3$ and $N_4$ are selected from the previewed endpoint plot.

The processed OES data is then calibrated using the PLS-DA process (step 1606). FIG. 18 is a detailed flowchart depicting a process for creating the X-block and y-block and using PLS regression to find a b-vector in accordance with an exemplary embodiment of the present invention. The calibration process begins by reading the processed data in spectra matrix X (step 1802) using sample numbers $N_1$, $N_2$, $N_3$ and $N_4$ (step 1804).

Since this particular embodiment is concerned with the processed OES data (step 1806), the X- and y-blocks are created for the processed periodic OES data in the unfolded spectra matrix X (step 1810). The training data set is arranged in an unfolded X-block created from data located in the regions of stable intensity values, e.g. between sample numbers $N_1$ and $N_2$ and between sample numbers $N_3$ and $N_4$, having one signal period of OES spectra per row. The y-block is then created for the class of stable intensity values using binary partitioning. The etch region is assigned a discriminate variable of "1." Regions other than the etch region are assigned a discriminate variable of "0." Thus, a y-block is created using binary partitioning such that a discriminate variable value of "1" is assigned to the region of intensity values for the etch process, corresponding to the $N_1$ to $N_2$ samples, and a discriminate value of "0" is assigned to all intensity values not in the class, corresponding to the $N_3$ to $N_4$ samples.

The data in the X-block and y-block are scaled (step 1812) and the PLS regression is then performed on the X- and y-blocks resulting in a b-vector (step 1814) Next, the $b_{lo}$, $b_{hi}$, $b_{lopeak}$ and $b_{hipeak}$ vectors are determined from the b-vector using $N_{lo}$ and $N_{hi}$ selections (step 1816) or by manually selecting indices of the b-vector. Each of the b, $b_{lo}$, $b_{hi}$, $b_{lopeak}$ and $b_{hipeak}$ vectors are then saved for use in processing real-time OES data for endpoint detection (step 1820).

As described above, prior to using the regression b-vector for processing real-time data it is validated by filtering the calibration data to produce an endpoint signal $y_0$. If the endpoint signal $y_0$ differs in appearance from the previewed endpoint plot, then the locations of $N_1$, $N_2$, $N_3$ and $N_4$ samples were probably chosen incorrectly and should be chosen again and reprocessed from step 1606. If endpoint signal $y_0$ compares favorably to the previewed endpoint signal, then any of the $b_{lo}$, $b_{hi}$, $b_{lopeak}$ and $b_{hipeak}$ from the regression matrix B can be relied upon for processing real-time data using one of the IP, IP-Ratio, Ratio or Peak Ratio methods (step 1610).

CHAMBER CLEANING

In addition to using partial least squares discriminant analysis for endpoint determination of a wafer in a production etch process, PLS-DA may be used for endpoint determination of chamber clean processes in accordance with other exemplary embodiments of the present invention. Chemical Vapor Deposition (CVD) is a technique for film deposition in semiconductor manufacturing. During this process, the film that is deposited on the wafer is also deposited on the interior walls of a CVD chamber. When the film on the walls becomes too thick, it will flake off and cause particle contamination of the wafers that are processed. To prevent this, CVD tool manufacturers include a chamber cleaning step for cleaning the interior of the CVD chamber after a specified number of wafers are processed. The cleaning step involves using a reactive plasma in the chamber. Film on the interior chamber walls is removed by a reaction with one or more components in the plasma, as it is in a wafer etching process.

Optical emission from the plasma is monitored to detect the endpoint of the cleaning step in a way that is similar to the method for the detection of the etch endpoint. The calibration data will show a stable post-etch region after all surfaces have cleared. Therefore, the $N_2$-to-$N_3$ region may be identified as before. However, during the chamber clean, it may be that there are multiple surfaces of different sizes, film thicknesses, and locations. These surfaces may clear at different times and there may not be a stable etch region. If there is a stable etch region, the $N_1$-to-$N_2$ region may be identified as described above. Otherwise, if there is not a stable region, $N_1$ and $N_2$ must be chosen in a novel way that characterizes the etch region. A single spectra or a region may be chosen where the etch is changing. In the later case, an average is obtained from the analysis for this $N_1$-to-$N_2$ region. The regression for the b-vector is performed as described above. The endpoint may be detected by Equations 4, 5, or 7. One of ordinary skill in the art would readily understand from the present invention that other variations are possible.

FAULT DETECTION

In accordance with still other exemplary embodiments of the present invention, PLS-DA is utilized for fault detection during, for example, a semiconductor fabricating process. In real-time or from wafer-to-wafer, we wish to know if a process or a process tool is running as expected. Further, if a failure is found, we wish to know what part of the tool or process has failed so that it can be repaired quickly. PLS-DA is capable of doing these two things by observing many sensors on a process tool in real-time. The real-time sensor readings, $G_{ij}$, from a semiconductor process tool can be measured at equal-time intervals during the process run. These are measurements of process parameters such as gas pressure, gas flow rate, throttle valve position, RF tuning capacitor position, RF power, temperature, etc. If appropriate, the intensity $I_{ij}$ of a spectra is also measured. Some of these parameters may not be measured, even though they have an effect on the process. These could include any of the previously mentioned parameters. To calibrate, C failure classes are identified for the tool or process. Calibration data is generated by measuring the parameters from a process and changing values of the parameters associated with the C failure modes. These parameters may be changed by changing their magnitudes or turning them off. For instance, if one of the failure modes is associated with a decrease in the flow rate of a gas, the flow rate of that gas is decreased during the calibration. Parameters associated with all C classes may be changed in one calibration set or one parameter may be changed in each of C calibration sets. The calibration data will then produce a V×C B-matrix, i.e. $Y_{ij}=X_{ik} \cdot B_{kj}$. The failure class j is then monitored with $y_j$, where $y_i=X_{ij} \cdot b_j$. In each case, PLS-DA will identify sensors that are sensitive to drift of a given process setting and generates a trend chart that changes when the process parameter drifts out of its normal setting.

The corresponding structures, materials, acts, and equivalents of all means or step plus function elements in the claims below are intended to include any structure, material, or act for performing the function in combination with other claimed elements as specifically claimed. While the present method has been described primarily in terms of synchronously detected periodic signal data, it may also be applied to other cases of data acquisition as described herein, including non-periodic signals, and asynchronously detected periodic signals.

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method creating a predictive model of an event in an etch process using partial least squares discriminant analysis (PLS-DA) comprising:

collecting calibration data for an etch process;

using at least a portion of the calibration data, identifying a feature associated with the event;

creating a predictor matrix, wherein the predictor matrix includes data for the feature associated with the event;

creating a response matrix, wherein the response matrix is comprised of a first discriminate variable value for the feature associated with the event; and finding a predictive model for the event by regressing the response matrix and the predictor matrix using PLS regression.

2. The method recited in claim 1, wherein the event is an endpoint event and the calibration data is collected using optical emission spectroscopy (OES), each OES data sample having intensity values for a plurality of simultaneously sampled discrete wavelengths, wherein identifying a feature associated with the event further comprises:

plotting an endpoint signal of intensity values from at least a portion of the OES data samples.

3. The method recited in claim 2 further comprises:

identifying a first region of stable intensity values on the endpoint signal associated with the endpoint event in an etch process; and selecting OES data samples associated with the first region of stable intensity values.

4. The method recited in claim 3, wherein the first region of stable intensity values on the endpoint signal representing an etch process occurring prior to the endpoint event.

5. The method recited in claim 3, wherein the first region of stable intensity values on the endpoint signal representing a post-etch process occurring subsequent to the endpoint event.

6. The method recited in claim 2 further comprises:

identifying a first region of stable intensity values on the endpoint signal;

identifying a second region of stable intensity values on the endpoint signal, wherein one of the first and second region of stable intensity values represents an etch process occurring prior to the endpoint event and the other of the first and second region of stable intensity values represents a post-etch process occurring subsequent to the endpoint event;

selecting OES data samples associated with the first region of stable intensity values and the second region of stable intensity values.

7. The method recited in claim 6, wherein the data for the feature associated with the event from the calibration data comprises OES data samples associated with one of the first and second region of stable intensity values.

8. The method recited in claim 6, wherein the first discriminate variable value represents the first region and a second discriminate variable value represents all other regions.

9. The method recited in claim 8, wherein the method further comprises:

calculating a resultant endpoint signal by applying the predictive model to the calibration data; and comparing the resultant endpoint signal to the endpoint signal from the at least a portion of the OES data.

10. The method recited in claim 8, wherein the OES data samples contain non-periodic intensity values, subsequent to collecting calibration data for an etch process the method further comprises:

processing the calibration data; and creating the predictor matrix further comprises:

arranging the OES data samples by having one OES data sample in each row of the predictor matrix.

11. The method recited in claim 10, wherein processing the calibration data further comprises:

removing OES data samples with startup or shutdown transients; and removing saturated wavelengths of OES data samples.

12. The method recited in claim 8, wherein the OES data samples are asynchronously sampled periodic intensity values, subsequent to collecting calibration data for an etch process the method further comprises:

filtering the periodic intensity values; and creating the predictor matrix further comprises:

arranging the OES data samples by having one OES data sample in each row of the predictor matrix.

13. The method recited in claim 8, wherein the OES data samples are synchronously sampled with a period of the intensity values, subsequent to collecting calibration data for an etch process the method further comprises:

processing the calibration data; and creating the predictor matrix further comprises:

arranging the OES data samples by having one period of OES data samples in each row of the predictor matrix.

14. The method recited in claim 13, wherein processing the calibration data further comprises:

removing OES data samples with startup or shutdown transients;

removing OES data samples with noise associated with the period;

selecting integral periods of OES data samples by removing periods having OES data samples associated with the first region of stable intensity values and OES data samples associated with another region; and removing saturated wavelengths of OES data samples.

15. The method recited in claim 1 further comprising:

detecting an event in a production etch process by filtering production data with the predictive model.

16. A method creating a predictive model of an endpoint of an etch process using partial least squares discriminant analysis (PLS-DA) comprising:

collecting data samples from a calibration wafer using optical emission spectroscopy (OES), each OES data sample having intensity values for a plurality of simultaneously sampled discrete wavelengths;

plotting an endpoint signal from the OES data samples using a plotting method for identifying a location of an endpoint transition;

identifying an etch region of stable intensity values and a post-etch region of stable intensity values on the endpoint signal;

creating a predictor matrix by arranging OES data samples associated with the etch region and the post-etch region by one OES sample in each row;

creating a response matrix with a first discriminate variable value for the OES data samples associated with the etch region and a second discriminate variable value for the OES data samples associated with the post-etch region;

finding a predictive model for the endpoint by regressing the response matrix and the predictor matrix using PLS regression; and filtering real-time data from a production wafer using the predictive model.

17. A method creating a predictive model of an endpoint of an etch process using partial least squares discriminant analysis (PLS-DA) comprising:

collecting data samples from a calibration wafer using optical emission spectroscopy (OES), each OES data sample having intensity values for a plurality of simultaneously sampled discrete wavelengths;

finding a time derivative of the optical emission spectroscopy (OES) data samples;

plotting an endpoint signal from the OES data samples using a plotting method for identifying a location of an endpoint transition;

identifying an etch region of stable intensity values, a transition region of evolving intensity values and a post-etch region of stable intensity values on the endpoint signal;

creating a predictor matrix by arranging OES sample derivative values associated with the etch region, the transition region and the post-etch region by one OES sample derivative value in each row;

creating a response matrix with a first discriminate variable value for OES sample derivative values associated with the transition region and a second discriminate variable value for all other OES sample derivative values;

finding a predictive model for the endpoint by regressing the response matrix and the predictor matrix using PLS regression; and filtering real-time data from a production wafer using the predictive model.

18. A method creating a predictive model of an endpoint of an etch process using partial least squares discriminant analysis (PLS-DA) comprising:

collecting data samples from a calibration wafer using optical emission spectroscopy (OES), each OES data sample having intensity values for a plurality of simultaneously sampled discrete wavelengths, wherein the OES data is synchronously sampled with a period of intensity data;

removing ambiguous and misleading OES data samples;

plotting an endpoint signal from the OES data samples using a plotting method for identifying a location of an endpoint transition;

identifying an etch region of stable intensity values and a post-etch region of stable intensity values on the endpoint signal;

creating a predictor matrix by arranging OES data samples associated with the etch region and the post-etch region by one period of OES samples in each row;

creating a response matrix with a first discriminate variable value for the OES data samples associated with the etch region and a second discriminate variable value for the OES data samples associated with the post-etch region;

finding a predictive model for the endpoint by regressing the response matrix and the predictor matrix using PLS regression; and filtering synchronously sampled real-time periodic data from a production wafer using the predictive model.

19. A method creating a predictive model of an event in an etch process using partial least squares discriminant analysis (PLS-DA) comprising:

collecting data samples from a calibration wafer, each data sample having a plurality simultaneously recorded readings, said event occurring in the data samples from a calibration wafer;

previewing an event plot from the data samples using previewing method for identifying a location of an event transition;

identifying the event transition region on the event plot;

creating a predictor matrix by arranging simultaneously recorded readings associated with the event transition region and simultaneously recorded readings not associated with the event transition region, by one simultaneously recorded reading in each row;

creating a response matrix with a first discriminate variable value for the simultaneously recorded readings associated with the event transition region and a second discriminate variable value simultaneously recorded readings not associated with the event transition region;

finding a predictive model for the event by regressing the response matrix and the predictor matrix using PLS regression; and filtering real-time data from a production wafer using the predictive model.

20. A method creating a predictive model of an event in a chamber cleaning process using partial least squares discriminant analysis (PLS-DA) comprising:

collecting calibration data for a chamber cleaning process;

using at least a portion of the calibration data, identifying a feature associated with the event;

creating a predictor matrix, wherein the predictor matrix includes data for the feature associated with the event;

creating a response matrix, wherein the response matrix is comprised of a first discriminate variable value for the feature associated with the event; and finding a predictive model for the event by regressing the response matrix and the predictor matrix using PLS regression.

21. The method recited in claim 20, wherein the event is an endpoint event and the calibration data is collected using optical emission spectroscopy (OES), each OES data sample having intensity values for a plurality of simultaneously sampled discrete wavelengths, wherein identifying a feature associated with the event further comprises:

plotting an endpoint signal of intensity values from at least a portion of the OES data samples.

22. The method recited in claim 21 further comprises:

identifying a first region of stable intensity values on the endpoint signal associated with the endpoint event in a chamber cleaning process; and selecting OES data samples associated with the first region of stable intensity values.

23. The method recited in claim 22, wherein the first region of stable intensity values on the endpoint signal represents a post-etch process after all interior surfaces of the chamber have cleared of film occurring subsequent to the endpoint event.

24. The method recited in claim 22, wherein the first region of stable intensity values on the endpoint signal represents an etch process occurring prior to the endpoint event.

25. The method recited in claim 22 further comprises:

identifying a first region of stable intensity values on the endpoint signal;

identifying a second region of stable intensity values on the endpoint signal, wherein one of the first and second region of stable intensity values represents an etch process occurring prior to the endpoint event and the other of the first and second region of stable intensity values represents a post-etch process after all interior surfaces of the chamber have cleared of film occurring subsequent to the endpoint event;

selecting OES data samples associated with the first region of stable intensity values and the second region of stable intensity values.

26. The method recited in claim 22 further comprises:

identifying a first region of stable intensity values on the endpoint signal representing a post-etch process after all interior surfaces of the chamber have cleared of film occurring subsequent to the endpoint event;

identifying a second region of non-stable intensity values on the endpoint signal representing an etch process for a plurality of interior surfaces of the chamber, wherein the second region is identified from a single spectra or a region of spectra having changing intensities.

27. A method creating a predictive model of a fault event in a semiconductor fabricating process using partial least squares discriminant analysis (PLS-DA) comprising:

collecting calibration data for a semiconductor fabricating process;

using at least a portion of the calibration data, identifying a feature associated with the fault event;

creating a predictor matrix, wherein the predictor matrix includes data for the feature associated with the fault event;

creating a response matrix, wherein the response matrix is comprised of a first discriminate variable value for the feature associated with the fault event; and finding a predictive model for the event by regressing the response matrix and the predictor matrix using PLS regression.

28. The method recited in claim 27, wherein collecting calibration data further comprises:

generating data from a measurement taken for a process parameter associated with a failure mode in the semiconductor fabricating; and changing the magnitude of the measurement.

29. The method recited in claim 28, wherein the measurement is one of gas pressure, gas flow rate, throttle valve position, RF tuning capacitor position, RF power, and temperature.

\* \* \* \* \*